United States Patent [19]

Egbertson et al.

[11] Patent Number: 5,494,921
[45] Date of Patent: Feb. 27, 1996

[54] FIBRINOGEN RECEPTOR ANTAGONISTS

[75] Inventors: Melissa S. Egbertson, Ambler; George D. Hartman, Lansdale; Laura A. Birchenough, North Wales, all of Pa.

[73] Assignee: Merck & Co., Inc., Rahway, N.J.

[21] Appl. No.: 307,966

[22] Filed: Sep. 16, 1994

[51] Int. Cl.$^6$ ............... A61K 31/445; C07D 211/32
[52] U.S. Cl. ............... 514/331; 514/428; 546/233; 548/572
[58] Field of Search ............... 546/233; 514/331, 514/428; 548/572

[56] References Cited

U.S. PATENT DOCUMENTS

| | | | |
|---|---|---|---|
| 5,227,490 | 7/1993 | Hartman et al. | 514/317 |
| 5,264,420 | 11/1993 | Duggan et al. | 514/19 |
| 5,272,158 | 12/1993 | Hartman et al. | 514/323 |
| 5,281,585 | 1/1994 | Duggan et al. | 514/79 |
| 5,292,756 | 3/1994 | Duggan et al. | 514/331 |
| 5,294,616 | 3/1994 | Duggan et al. | 514/255 |
| 5,321,034 | 6/1994 | Duggan et al. | 514/323 |
| 5,334,596 | 8/1994 | Hartman et al. | 514/301 |
| 5,340,798 | 8/1994 | Nutt et al. | 514/18 |
| 5,344,957 | 9/1994 | Bovy | 560/35 |

FOREIGN PATENT DOCUMENTS

| | | |
|---|---|---|
| 2271567 | 4/1994 | United Kingdom . |
| 94/08577 | 4/1994 | WIPO . |
| 94/08962 | 4/1994 | WIPO . |
| 94/18981 | 9/1994 | WIPO . |

Primary Examiner—C. Warren Ivy
Assistant Examiner—Evelyn Huang
Attorney, Agent, or Firm—Richard S. Parr; Melvin Winokur

[57] ABSTRACT

Fibrinogen receptor antagonists having the formula

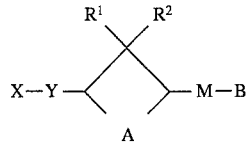

for example

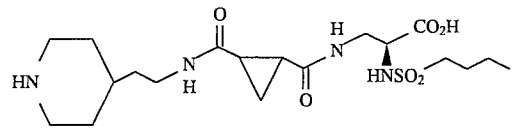

8 Claims, No Drawings ated Merck & Co., Inc., and published on Jul. 17, 1991 discloses linear polypeptide fibfinogen receptor antagonists. Eur. Pat. App. No. 90101404.3 discloses compounds of the $R^1$—A—$(W)_a$—X—$(CH_2)_b$—$(Y)_c$—B—Z—

FIBRINOGEN RECEPTOR ANTAGONISTS

BACKGROUND OF THE INVENTION

The invention relates generally to modulating cell adhesion and to inhibiting the binding of fibrinogen and other proteins to blood platelets, and inhibiting the aggregation of blood platelets specifically to the gp IIb/IIIa fibrinogen receptor site. Fibrinogen is a glycoprotein present in blood plasma that participates in platelet aggregation and in fibrin formation. Platelets are cell-like anucleated fragments, found in the blood of all mammals, that also participate in blood coagulation. Interaction of fibrinogen with the IIb/IIIa receptor site is known to be essential for normal platelet function.

When a blood vessel is damaged by an injury or other causative factor, platelets adhere to the disrupted subendothethial surface. The adherent platelets subsequently release biologically active constituents and aggregate. Aggregation is initiated by the binding of agonists, such as thrombin, epinephrine, or ADP to specific platelet membrane receptors. Stimulation by agonists results in exposure of latent fibrinogen receptors on the platelet surface, and binding of fibrinogen to the glycoprotein IIb/IIIa receptor complex.

Attempts have been made to use natural products and synthetic peptides to determkne the mechanism of adhesion and platelet aggregation. For example, Rouslahti and Pierschbacher in *Science*, 238, 491–497 (1987), describe adhesive proteins such as fibronectin, vitronectin, osteopontin, collagens, thrombospondin, fibrinogen, and von Willebrand factor that are present in extracellular matrices and in blood. The proteins contain the tripeptide arginine-glycine-aspartic acid (RGD) as their glycoprotein IIb/IIIa recognition site. These argininne-glycine-aspartic acid containing tripeptides are recognized by at least one member of a family of structurally related receptors, integrins, which are heterodimeric proteins with two membrane-spanning subunits. The authors state that the conformation of the tripeptide sequence in the individual proteins may be critical to recognition specificity.

Cheresh in *Proc. Nat'l Acad. Sci*, U.S.A., 84, 6471–6475, (1987), describes an Arg-Gly-Asp directed adhesion receptor expressed by human endothethial cells that is structurally similar to the IIb/IIIa complex on platelets but is antigenically and functionally distinct. This receptor is directly involved in endothelial cell attachment to fibrinogen, von Willebrand factor, and vitronectin.

Pierschbacher and Rouslahti, in *J. of Biol Chem.*, 262, (36), 17294–17298 (1987) hypothesized that the Arg-Gly-Asp sequence alone would be a sufficient signal for receptor recognition and binding and that, therefore, the conformation of the tri-peptide sequence would be determinative. Various synthetic peptides were produced and the authors concluded that the sterochemical conformation of Arg-Gly-Asp as influenced by enantiomeric substitutions or additions to this sequence significantly influenced receptor-ligand interaction. The authors further showed that cyclizati on of a decapeptide by forming a disulfide bridge between non-terminal residues Pen and Cys, rendered the peptide much less effective at inhibiting attachment to fibronectin.

In *Proc. Nat'l Acad. Sci.* U.S.A., 81, 5985–5988 (1984), the same authors describe tetrapeptide variants of the cell recognition site of fibronectin that retain attachment-promoting activity. Peptides having a tetrapeptide recognition site are described in U.S. Pat. Nos. 4,589,881 and 4,614,517.

A number of large polypeptide fragments in the cell-binding domain of fibronectin have cell-attachment activity. For example, see U.S. Pat. Nos. 4,517,686, 4,661,111 and U.S. Pat. No. 4,578,079.

Ruggeri et al., *Proc. Nat'l Acad. Sci.* U.S.A., 83, 5708–5712 (1986) explore a series of synthetic peptides designed in lengths to 16 residues, that contain RGD and a valine attached to the aspartic acid residue of RGD that inhibit fibrinogen binding to platelets. See also Koczewiak et al., *Biochem.* 23, 1767–1774 (1984); Ginsberg et al., *J. Biol. Chem.* 260(7), 3931–3936 (1985); and Hayerstick et al., *Blood* 66(4), 946–952 (1985). Other inhibitors are disclosed in Eur. Pat. App. Nos. 275,748 and 298,820.

A number of low molecular weight polypeptide factors have been isolated from snake venom. These factors apparently have high affinity for the gp IIb/IIIa complex. For example, Huang et al., *J. Biol Chem.*, 262, 16157–16163 (1987); Huang etal., *Biochemistry* 28, 661–666 (1989) describe the primary structure of the venom trigramin which is a 72 amino acid polypeptide that contains the RGD subunit. Echistatin is another compound which has high affinity for the gp IIb/IIIa complex. This polypeptide contains 49 amino acids and has the RGD subunit and various disulfide bridges. Gan et al., *J. Biol, Chem.*, 263, 19827–19832 (1988). See also, Dennis et al., *Proc. Nat'l Acad. Sci.* USA, 87, 2471–2475 (1989). However, these snake venom factors also have high affinity for other members of the adhesive protein receptor family including the vitronectin and fibronectin receptors so are not selective for the gp IIb/IHa complex.

While it is known that the tripeptide sequence Arg-Gly-Asp is present in certain polypeptides that can duplicate or inhibit the cell attachment-promoting effects of fibronectin and vitronectin, the tripeptide Arg-Gly-Asp has low activity. At present, there is little understanding of how other amino acids coupled to this sequence influence binding specificity. U.S. Pat. No 5,023,233, assigned to Merck & Co., Inc., discloses small cyclic hexapeptides which contain the sequence Arg-Gly-Asp and are useful platelet aggregation inhibitors. U.S. Pat. No. 5,037,808 discloses the use of indolyl platelet-aggregation inhibitors which are believed to act by antagonizing interactions between fibrinogen and/or extracellular matrix proteins and the platelet gp IIb/IHa receptor. U.S. Pat. No. 5,037,808 discloses guanidino peptide mimetic compounds that retain an Asp residue which inhibit platelet aggregation. The application PCT/US90/02746 describes the use of antibody-poly-peptide conjugates wherein said polypeptides contain the Arg-Gly-Asp (RGD) sequence.

The application PCT/US91/00564 discloses the use of large cyclic peptides containing RGD flanked by proline residues which are platelet aggregation inhibitors. The application PCT/US90/03788 discloses small cyclic platelet aggregation inhibitors which are synthetic cyclic pentapeptides containing the tripeptide sequence Arg-Gly-Asp and a thioether linkage in the cycle. The application PCT/US90/05367 published May 2, 1991 also discloses the use of peptides and pseudopeptides such as N-amidino-piperidine-3-carboxylglycyl-L-aspanyl-L-valine that inhibit platelet aggregation and thrombus fonnation in mammalian blood. The application Eur. Pat. App. No. 91103462.7 discloses linear compounds which can include internal piperazinyl or piperidinyl derivatives. Eur. Pat. App. No. 91300179.8, assigned to Merck & Co., Inc., and published on Jul. 17, 1991 discloses linear polypeptide fibfinogen receptor antagonists. Eur. Pat. App. No. 90101404.3 discloses compounds of the $R^1$—A—$(W)_a$—X—$(CH_2)_b$—$(Y)_c$—B—Z—

COOR wherein $R^1$ is a guandidino or amidino moiety and A and B are chosen from specific monosubstituted aryl or heterocyclic moieties.

While a multitude of compounds or peptide analogs believed to inhibit platelet aggregation by inhibiting binding to a blood platelet by fibrinogen are known, the present invention provides novel fibrinogen receptor antagonists that have significant binding activity and are, therefore, useful for the reasons stated herein. A number of very serious diseases and disorders involve hyperthrombotic complications which lead to intravascular thrombi and emboli. Myocardial infarction, stroke, phlebitis and a number of other serious conditions create the need for novel and effective fibrinogen receptor antagonists.

SUMMARY OF THE INVENTION

The invention is a fibrinogen receptor antagonist of the formula:

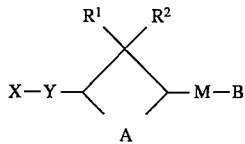

and pharmaceutically acceptable salts thereof, and esters thereof, wherein
X is chosen from:

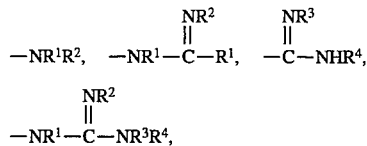

and a 4- to 10- membered mono- or polycyclic aromatic or nonaromatic ring system containing 0, 1, 2, 3 or 4 heteroatom selected from N, O and S, said heteroatoms either unsubstituted or substituted with $R^1$, $R^2$, $R^3$, or $R^4$, wherein $R^1$, $R^2$, $R^3$ and $R^4$ are independently selected from the group consisting of:
hydrogen,
$C_{1-10}$ alkyl,
aryl $C_{0-8}$ alkyl,
oxo,
thio,
amino $C_{0-8}$ alkyl, $C_{1-3}$ acylamino $C_{0-8}$ alkyl,
$C_{1-6}$ alkylamino $C_{0-8}$ alkyl,
$C_{1-6}$ dialkylamino $C_{0-8}$ alkyl,
$C_{1-4}$ alkoxy $C_{0-6}$ alkyl,
carboxy $C_{0-6}$ alkyl, $C_{1-3}$ alkoxycarbonyl $C_{0-6}$ alkyl,
carboxy $C_{0-6}$ alkyloxy and
hydroxy $C_{0-6}$ alkyl;
Y and M are independently chosen from:

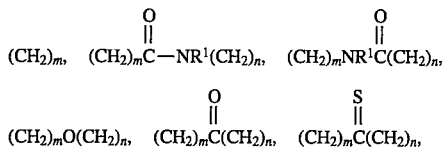

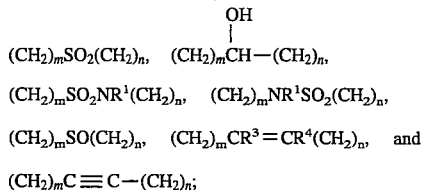

A is chosen from:

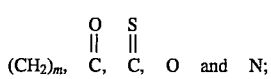

m and n, wherein m is independently selected for Y, M and A, are integers independently chosen from 0–6;
B is chosen from:

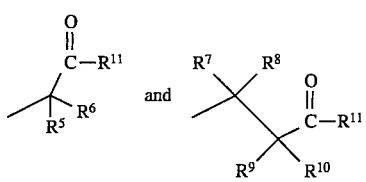

wherein $R^5$, $R^6$, $R^7$, $R^8$, $R^9$ and $R^{10}$ are independently chosen from:
hydrogen,
flourine,
$C_{1-8}$ alkyl,
hydroxyl,
hydroxy $C_{1-6}$ alkyl,
carboxy $C_{0-6}$ alkyl,
$C_{1-6}$ alkyloxy $C_{0-6}$ alkyl,
$C_{1-6}$ alkylcarbonyl $C_{0-6}$ alkyl,
$C_{3-8}$ cycloalkyl $C_{0-6}$ alkyl,
aryl $C_{0-6}$ alkylcarbonyl $C_{0-6}$ alkyl,
aryl $C_{0-6}$ alkyl,
$C_{1-6}$ alkylcarbonyloxy $C_{0-6}$ alkyl,
$C_{0-6}$ alkylamino $C_{0-6}$ alkyl,
aryl $C_{0-6}$-alkylamino-$C_{0-6}$-alkyl,
$C_{0-6}$ dialkylamino $C_{0-6}$ alkyl,
aryl $C_{0-6}$alkylcarbonyloxy $C_{0-6}$ alkyl,
C1–8 alkylsulfonylamino $C_{0-6}$ alkyl,
$C_{1-6}$ alkylaminocarbonyloxy $C_{0-6}$ alkyl,
aryl $C_{0-6}$-alkylaminocarbonyloxy $C_{0-6}$alkyl,
aryl $C_{0-6}$ alkylsulfonylamino $C_{0-6}$ alkyl,
$C_{1-8}$ alkyloxycarbonyalmino $C_{0-8}$ alkyl,
aryl $C_{0-8}$ alkyloxycarbonylamino $C_{0-8}$ alkyl,
$C_{1-8}$ alkylcarbonylamino $C_{0-6}$ alkyl,
aryl $C_{0-6}$ alkylcarbonylamino $C_{0-6}$ alkyl,
$C_{0-8}$ alkylaminocarbonyl $C_{0-6}$ alkyl,
aryl $C_{0-8}$ alkylaminocarbonyl $C_{0-6}$ alkyl,
$C_{1-8}$ alkylaminocarbonylamino $C_{0-6}$ alkyl,
aryl $C_{0-8}$ alkylaminocarbonylamino $C_{0-6}$ alkyl,
$C_{0-8}$ alkylaminosulfonylamino $C_{0-6}$ alkyl,
aryl $C_{0-8}$ alkylaminosulfonylamino $C_{0-6}$ alkyl,
$C_{1-6}$ alkylsulfonyl $C_{0-6}$ alkyl,
aryl $C_{0-6}$ alkylsulfonyl $C_{0-6}$ alkyl,
$C_{1-6}$ alkylcarbonyl $C_{0-6}$ alkyl, aryl $C_{0-6}$ alkylcarbonyl $C_{0-6}$ alkyl,
$C_{1-6}$ alkylthiocarbonylamino $C_{0-6}$ alkyl,
aryl $C_{0-6}$ alkylthiocarbonylamino $C_{0-6}$ alkyl,
wherein alkyl groups may be unsubstimted or substituted with one or more substituents selected from $R^1$ and $R^2$, and

C—AA where AA is an L- or D- amino acid, or its corresponding ester, connected through an amide linkage; and
$R^{11}$ is chosen from:
  hydroxy,
  $C_{1-8}$ alkyloxy,
  aryl $C_{0-6}$ alkyloxy,
  $C_{1-8}$ alkylcarbonyloxy $C_{1-4}$ alkyloxy,
  aryl $C_{1-8}$ alkylcarbonyloxy $C_{1-4}$ alkyloxy,
  $C_{0-6}$ alkylaminocarbonylmethyl, and
  $C_{0-6}$ dialkylaminocarbonylmethyl,
and L- or D-amino acid joined by an amide linkage and wherein the carboxylic acid moiety of said amino acid is as the free acid or is esterified by $C_{1-6}$ alkyl.

One class of compounds of the invention has the formula

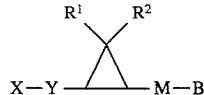

and pharmaceutical salts thereof, and esters thereof, where X is chosen from:

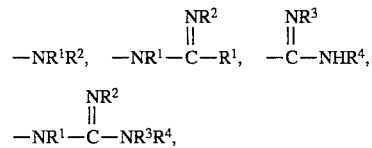

and a 4- to 10- membered mono- or polycyclic aromatic or nonaromatic ring system containing 0, 1, 2, 3 or 4 heteroatoms selected from N, O and S, said heteroatoms either unsubstituted or substituted with $R^1$, $R^2$, $R^3$ or $R^4$, wherein $R^1$, $R^2$, $R^3$ and $R^4$ are independently selected from the group consisting of:
  hydrogen,
  $C_{1-10}$ alkyl,
  aryl $C_{0-8}$ alkyl,
  oxo,
  thio,
  amino $C_{0-8}$ alkyl, $C_{1-3}$ acylamino $C_{0-8}$ alkyl,
  $C_{1-6}$ alkylamino $C_{0-8}$ alkyl,
  $C_{1-6}$ dialkylamino $C_{0-8}$ alkyl,
  $C_{1-4}$ alkoxy $C_{0-6}$ alkyl,
  carboxy $C_{0-6}$ alkyl, $C_{1-3}$ alkoxycarbonyl $C_{0-6}$ alkyl,
  carboxy $C_{0-6}$ alkyloxy and
  hydroxy $C_{0-6}$ alkyl;
Y and M are independently chosen from:

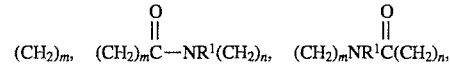

-continued

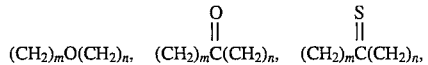

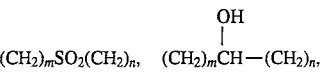

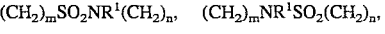

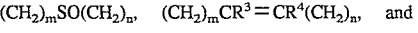

m and n, wherein m is independently selected for Y, M and A, are integers independently chosen from 0–6;
B is chosen from:

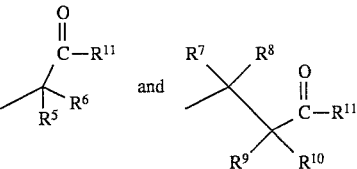

wherein $R^5$, $R^6$, $R^7$, $R^8$, $R^9$ and $R^{10}$ are independently chosen from:
  hydrogen,
  flourine,
  $C_{1-8}$ alkyl,
  hydroxyl,
  hydroxy $C_{1-6}$ alkyl,
  carboxy $C_{0-6}$ alkyl,
  $C_{1-6}$ alkyloxy $C_{0-6}$ alkyl,
  $C_{1-6}$ alkylcarbonyl $C_{0-6}$ alkyl,
  $C_{3-8}$ cycloalkyl $C_{0-6}$ alkyl,
  aryl $C_{0-6}$ alkylcarbonyl $C_{0-6}$ alkyl,
  aryl $C_{0-6}$ alkyl,
  $C_{1-6}$ alkylcarbonyloxy $C_{0-6}$ alkyl,
  $C_{0-6}$ alkylamino $C_{0-6}$ alkyl,
  aryl $C_{0-6}$-alkylamino-$C_{0-6}$ alkyl,
  $C_{0-6}$ dialkylamino $C_{0-6}$ alkyl,
  aryl $C_{0-6}$alkylcarbonyloxy $C_{0-6}$ alkyl,
  $C_{1-8}$ alkylsulfonylamino $C_{0-6}$ alkyl,
  $C_{1-6}$ alkylaminocarbonyloxy $C_{0-6}$ alkyl,
  aryl $C_{0-6}$-alkylaminocarbonyloxy $C_{0-6}$ alkyl,
  aryl $C_{0-6}$ alkylsulfonylamino $C_{0-6}$ alkyl,
  $C_{1-8}$ alkyloxycarbonylamino $C_{0-8}$ alkyl,
  aryl $C_{0-8}$ alkyloxycarbonylamino $C_{0-8}$ alkyl,
  $C_{1-8}$ alkylcarbonylamino $C_{0-6}$ alkyl,
  aryl $C_{0-6}$ alkylcarbonylamino $C_{0-6}$ alkyl,
  $C_{0-8}$ alkylaminocarbonyl $C_{0-6}$ alkyl,
  aryl $C_{0-8}$ alkylaminocarbonyl $C_{0-6}$ alkyl,
  $C_{1-8}$ alkylaminocarbonylamino $C_{0-6}$ alkyl,
  aryl $C_{0-8}$ alkylaminocarbonylamino $C_{0-6}$ alkyl,
  $C_{0-8}$ alkylaminosulfonylamino $C_{0-6}$ alkyl,
  aryl $C_{0-8}$ alkylaminosulfonylamino $C_{0-6}$ alkyl,
  $C_{1-6}$ alkylsulfonyl $C_{0-6}$ alkyl,
  aryl $C_{0-6}$ alkylsulfonyl $C_{0-6}$ alkyl,
  $C_{1-6}$ alkylcarbonyl $C_{0-6}$ alkyl,
  aryl $C_{0-6}$ alkylcarbonyl $C_{0-6}$ alkyl,
  $C_{1-6}$ alkylthiocarbonylamino $C_{0-6}$ alkyl, aryl $C_{0-6}$ alkylthiocarbonylamino $C_{0-6}$ alkyl,
wherein alkyl groups may be unsubstituted or substituted with one or more substituents selected from $R^1$ and $R^2$, and $$\overset{O}{\underset{}{\overset{\|}{C}}}-AA$$

where AA is an L- or D- amino acid, or its corresponding ester, connected through an amide linkage; and $R^{11}$ is chosen from:

hydroxy,
$C_{1-8}$ alkyloxy,
aryl $C_{0-6}$ alkyloxy,
$C_{1-8}$ alkylcarbonyloxy $C_{1-4}$ alkyloxy,
aryl $C_{1-8}$ alkylcarbonyloxy $C_{1-4}$ alkyloxy, and
and L- or D-amino acid joined by an amide linkage and wherein the carboxylic acid moiety of said amino acid is as the free acid or is esterified by $C_{1-6}$ alkyl.

DETAILED DESCRIPTION OF THE INVENTION

The table below identifies specific embodiments of this class of compounds, and their ability to inhibit aggregation:

TABLE 1

| Structure | IC$_{50}$ Plaggin |
|---|---|
|  1:1 mixture trans diasteromers | 0.21 μM |
| 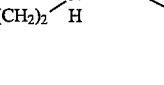 | 0.077 μM |
| 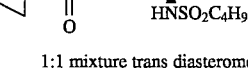 | 0.58 μM |
|  | 1.2 μM |
| 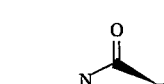 | 3.5 μM |
| 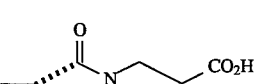 | 17 μM |
| 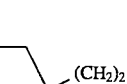 1:1 mixture of trans diasteromers | 0.14 μM |

TABLE 1-continued

| | $IC_{50}$ Plaggin |
|---|---|
| 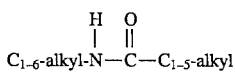 | 17 μM |

The term "pharmaceutically acceptable salts" shall mean non-toxic salts of the compounds of this invention which are generally prepared by reacting the free base with a suitable organic or inorganic acid. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, parnaote, palmitate, panthothenate, phosphate/diphosphate, polygalacturonate, salicylate, stearate, subacetate, succinate, tanhate, tartrate, teoclate, tosylate, triethiodide, valerate.

The compounds of the present invention are chiral; included within the scope of the present invention are racemic mixtures and separated enantiomers of the general formula. Furthermore all diastereoimers, including E, Z isomers, of the general formula are included in the present scope. Furthermore, hydrates as well as anhydrous compositions and polymorphs of the general formula are within the present invention.

Prodrugs, such as ester derivatives of described compounds, are compound derivatives which, when absorbed into the bloodstream of a warm-blooded animal, cleave in such a manner as to release the drug form and pennit the drag to afford improved therapeutic efficacy.

The term "pharmaceutically effective amount" shall mean that amount of a drug or pharmaceutical agent that will elicit the biological or medical response of a tissue, system or animal that is being sought by a researcher or clinician. The term "anti-coagulant" shall include heparin, and warfarin. The tenn "thrombolytic agent" shall include agents such as streptokinase and tissue plasminogen activator. The term "platelet anti-aggregation agent" shall include agents such as aspirin and dipyridamole.

The term "alkyl" means straight or branched alkane, alkene or alkyne.

The term "aryl" means a 5- or 6-membered aromatic ring containing 0, 1, or 2 heteroatoms selected from O, N, and S.

The terms "alkyloxy" or "alkoxy" include an alkyl portion where alkyl is as defined above.

The terms "arylalkyl" and "alkylaryl" include an alkyl portion where alkyl is as defined above and to include an aryl portion where aryl is as defined above. The $C_{0-n}$ or $C_{1-n}$ designation where n may be an integer from 1–10 or 2–10 respectively refers to the alkyl component of the arylalkyl or alkylaryl unit.

The term "halogen" includes fluorine, chlorine, iodine and bromine.

The term "oxy" means an oxygen (O) atom. The term "thio" means a sulfur (S) atom. Under standard nonmenclature used throughout this disclosure, the terminal portion of the designated side chain is described first followed by the adjacent functionality toward the point of attachment. For example, a $C_{1-6}$ alkyl substituted with $C_{1-5}$ alkylcarbonylamino is equivalent to $$C_{1-6}\text{-alkyl-N}\overset{H}{\underset{}{\,}}-\overset{O}{\underset{}{C}}-C_{1-5}\text{-alkyl}$$

In the schemes and examples below, various reagent symbols have the following meanings:
BOC(or Boc): t-butyloxycarbonyl.
Pd-C: Palladium on activated carbon catalyst.
DMF: Dimethylformamide.
DMSO: Dimethylsulfoxide.
CBZ: Carbobenzyloxy.
$CH_2Cl_2$: Methylene chloride.
$CHCl_3$: chloroform.
EtOH: ethanol.
MeOH: methanol.
EtOAc: ethyl acetate.
HOAc: acetic acid.
BOP: Benzotriazol-1-yloxytris(dimethylamino)-phosphonium, hexafluorophosphate.
EDC: 1-(3-Dimethylaminopropyl)-3-ethylcarbodiimide hydrochloride.
Oxone: potassium peroxymonosulfate.
LDA: Lithium diisopropylamide.

X, a terminal basic moiety of compound of the invention, is exemplified by heterocyclic rings such as

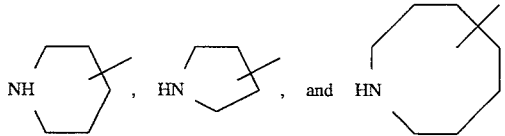

and heteroaromatic rings such as

as well as amino, amidino, and guanadino moieties.

The examples describe strategies for preparing compounds where X is a piperidinyl group, using source materials such as

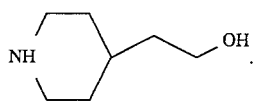

Similar strategies can be employed for incorporating

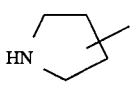

using proline as a source material,

using pyridine-4-carboxylic acid as a source material, and

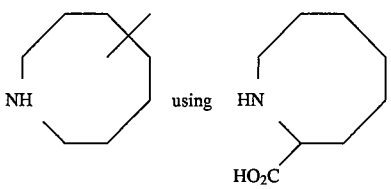

as a source material.

Preparation of Methyl 3-amino-2(S)-n-butylsulfonylaminopropionate (1–6)

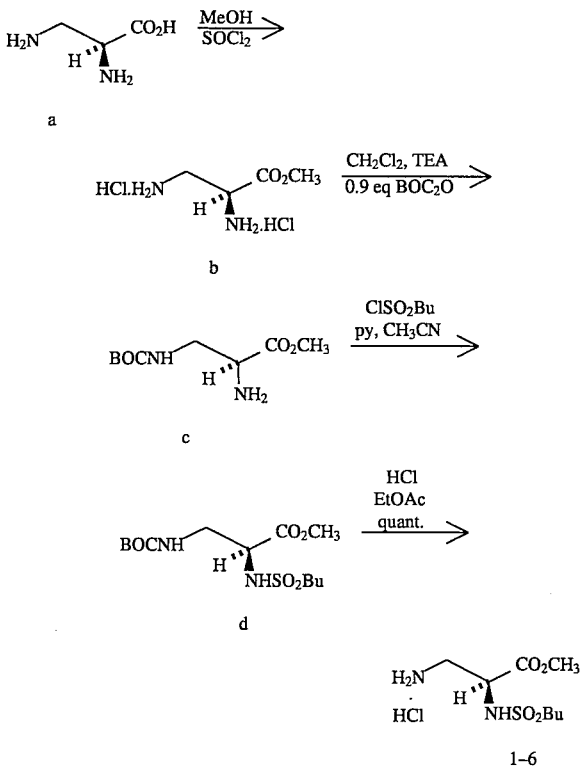

Methyl 2(S), 3-Diaminopropanoate (b)

Methanol (400 mL) was cooled to 0° C. and thionyl chloride (217 mL, 3.0 moles, 20 eq) was added dropwise under argon. After addition was completed, the solution was warmed to a room temperature for 20 minutes. 2(S), 3-Diaminopropanoic acid a (Schweizerhall) (20 g, 0.243 mole) was crushed to a fine powder and added to the solution. The reaction was heated to reflux for 48 hours, at which time TLC showed a small amount of starting material remaining. An additional portion of methanol (100 mL) and thionyl chloride (72 mL) was prepared as before and added to the reaction at room temperature; the reaction was then stirred overnight at room temperature. The reaction was worked up by removal of solvent at 40° C. in vacuo, to provide b.

$R^f$ 0.72 (9:1:1 EtOH/$H_2O$/$NH_4OH$). $^1H$ NMR (400 MHz, $D_2O$) δ5 4.55 (dd, J=5.4, 8.2 Hz, 1H), 3.92 (s, 3H), 3.64 (dd, J=8.2, 13.8 Hz, 1H), 3.55 (dd, J=5.4, 13.8 Hz, 1H).

Methyl 2(S)-3(N-t-Butyloxycarbonyl)diaminopropanoate (c)

b (6.0 g, 31.5 mmoles) was crushed to a fine powder, suspended in 1L of $CH_2Cl_2$ and cooled to −78° C. under argon. Triethylamine (17.5 mL, 0.126 moles, 4 eq) was added dropwise; the solution gradually became homogenous. Di-t-butyldicarbonate (6.18 g, 2.83 mmoles, 0.9 eq) was dissolved in 50 mL $CH_2Cl_2$ and added dropwise to the solution. After the addition was completed, the reaction was placed in an ice bath and stirred for 1½ hours. The reaction was transferred to a separatory funnel and extracted with 3×50 mL of 10% $KHSO_4$ solution. The aqueous layer was washed with 3×10 mL of $CH_2Cl_2$, then basified with saturated $NaHCO_3$ and 3N NaOH solution to pH10 and extracted with 10×100 mL of $CH_2Cl_2$. The organic layer was dried with $Na_2SO_4$, filtered and evaporated to give 4.9 g of a pale yellow oil. Column chromatography in 2.5% MeOH/EtOAc gave c as an oil.

$R^f$ 0.39 (5% MeOH/EtOAc). $^1H$ NMR (400 MHz, $CDCl_3$) δ5 5.0 (bs, 1H), 3.72 (s, 3H), 3.56 (t, J=5.7 Hz, 1H), 3.46 (m, 1H), 3.23 (m, 1H), 1.55 (bs, 2H), 1.42 (s, 9H).

Methyl 2(S)-(N-Butylsulfonylamino)-3-(N-t-butyloxycarbonylamino)-diaminopropionic (d)

c was dissolved in acetonitrile (100 mL) and three portions of n-butylsulfonly chloride (1.62 mL, 12.5 mmoles), and pyridine (1.0 mL, 12.5 mmoles) were added over a period of three hours. The reaction was allowed to stir overnight, concentrated to ¼ its original volume, then diluted with 100 mL EtOAc and washed with 10% $KHSO_4$ (5×20 mL), dried with brine and $MgSO_4$, filtered and evaporated. Column chromatography in 20%–40% EtOAc/hexanes gave d as an oil.

$R^f$ 0.6 (5% MeOH/$CHCl_3$). $^1H$ NMR (400 MHz, $CDCl_3$) δ5.48 (Bd, 1H), 4.9 (Bs, 2H), 4.22 (m, 1H), 3.8 (s, 3H), 3.53 (m, 2H), 3.02 (m, 2H), 1.80 (m, 2H), 1.46 (m, 2H), 1.43 (s, 9H), 0.94 (t, J=7.4 Hz, 3H).

2(S)-(N-Butylsulfonylamino)-3-aminopropionic acid methyl ester hydrochloride (1–6)

d (2.0 g, 5.9 mmoles) was dissolved in 30 mL of EtOAc and cooled to −40° C. HCl gas was bubbled through the solution until it was saturated, then the reaction was warmed to 0° C. and stirred for 1 hour. The excess HCl was removed under vacuum at room temperature and the reaction was concentrated at 35° C. to give 1–6.

$R^f$ 0.6 (9:1 EtOH/$H_2O$). $^1H$ NMR (400 MHz, $CDCl_3$) δ0.1 (bs, 2H), 7.2 (m, 1H), 4.65 (m, 1H), 3.82 (s, 3H), 3.65 (m, 1H), 3.54 (m, 2H), 3.20 (bs, 2H), 1.8 (m, 2H), 1.45 (m, 2H), 0.95 (t, J=7.3 Hz).

SCHEME 1
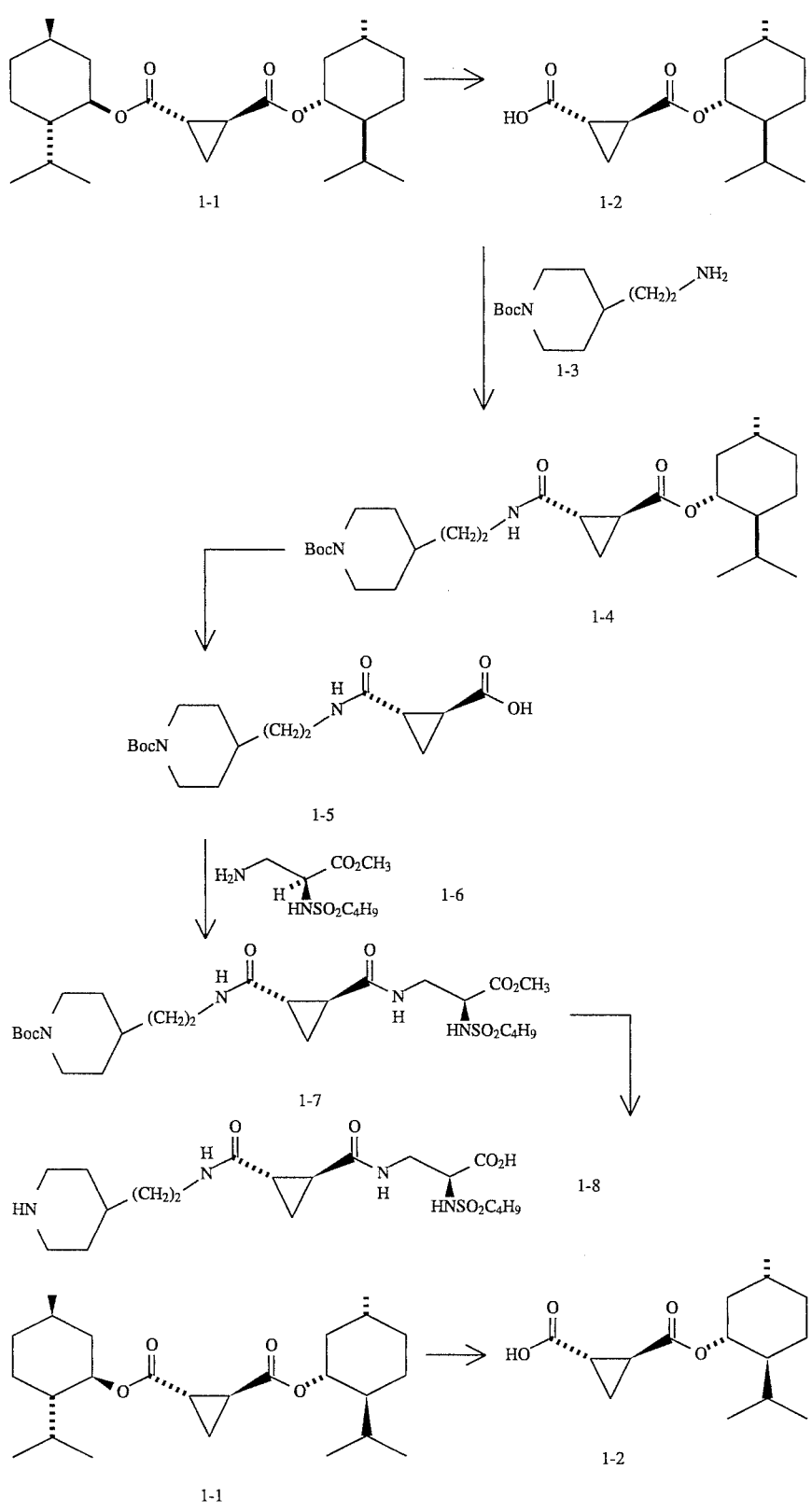

Mono-(1R,2S,5R)-(–)-menthyl- 1 (S),2(S)-cyclopropane dicarboxylate (1–2)

Bis-L-menthyl 1(S),2(S) cyclopropane dicarboxylate (1—1, *Org. Syn.* 67, p. 76–85) (1.3 g, 3.2 mmol) was suspended in 5 mL 9:1 CH₃OH/H₂O and treated with KOH (0.18 g, 3.2 mmol) at 65° C. for 5 hours. The reaction was diluted with 10 mL H₂O and extracted with 3×20 mL ether, then acidified to pH 2 with 10% HCl and extracted with ether. The organic layer was dried with Na₂SO₄, filtered and concentrated to give 1–2 as a yellow oil.

$R_f$ (97:3:1 CHCl₃/CH₃OH/HOAc) 0.26. ¹H NMR (300 MHz, CDCl₃) δ4.65 (m, 1H), 2.15 (m, 2H), 1.95 (d, 1H), 1.8 (m, 1H), 1.65 (d, 2H), 1.4 (m, 4H), 1.1–0.8 (m, 3H), 0.88 (s, 3H), 0.8 (s, 3H), 0.73 (d, 3H).

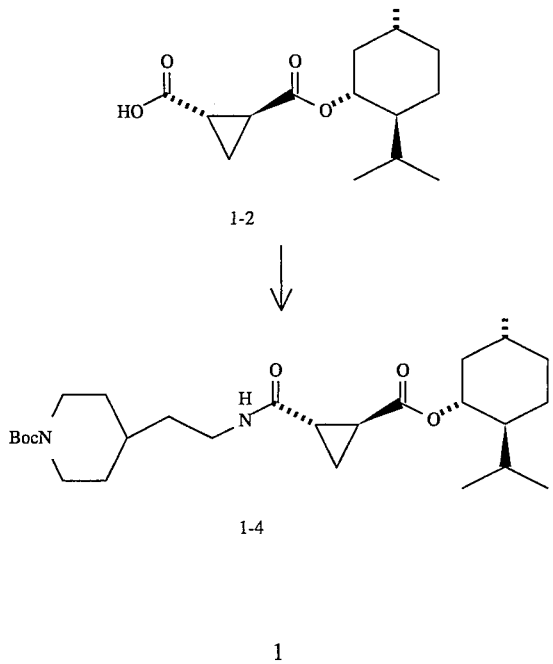

1 (S)-[(2-(N-t-Butyloxycarbonylpiperidin-4-yl)ethyl)-acetamido]-2(S)-(L-menthylcarboxylate)cyclopropane (1–4)

Compound 1–2 (0.51 g, 1.92 mmol) was suspended in 5 mL acetonitrile and treated with amine 1–3 (source Hartman et al., WO 94/08577, page 47), triethyl-amine 0.62 mL (4.5 mmol) and BOP reagent (1.02 g, 2.3 mmol) at room temperature for 18 hours. The reaction was concentrated, dissolved in EtOAc and extracted with 10% KHSO₄ and brine. The organic layer was concentrated and purified by flash chromatography on silica eluting with 25% acetone/hexanes to give 1–4 as a white solid.

$R_f$ (25% acetone/hexane) 0.26. ¹H NMR (300 MHz, CDCl₃) δ6.5 (m, 1H), 4.75 (m, 1H), 4.15 (d, 2H), 3.4 (m, 2H), 2.75 (t, 2H), 2.2 (m, 1H), 2.0 (m, 3H), 1.8 (d, 3H), 1.6 (s, 9H), 1.5 (m, 3H), 1.4 (m, 2H), 1.1–0.9 (m, 4H), 1.0 (s, 3H), 0.95 (s, 3H) 0.85 (d, 3H).

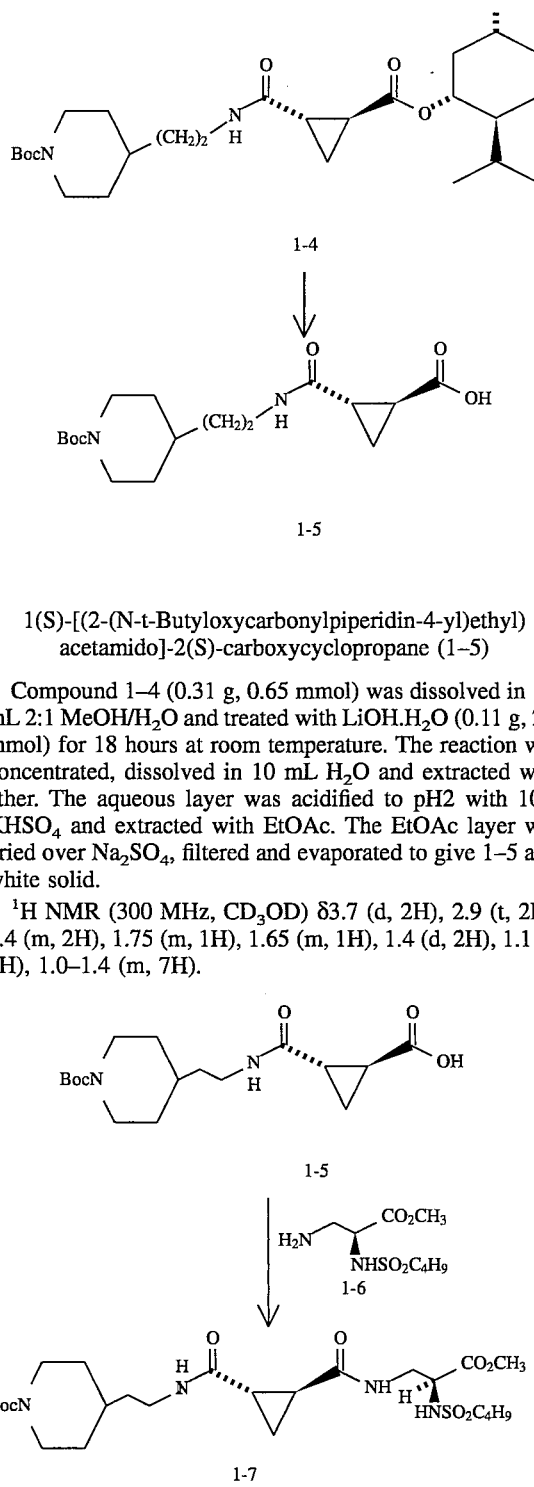

1(S)-[(2-(N-t-Butyloxycarbonylpiperidin-4-yl)ethyl) acetamido]-2(S)-carboxycyclopropane (1–5)

Compound 1–4 (0.31 g, 0.65 mmol) was dissolved in 1.5 mL 2:1 MeOH/H₂O and treated with LiOH.H₂O (0.11 g, 2.6 mmol) for 18 hours at room temperature. The reaction was concentrated, dissolved in 10 mL H₂O and extracted with ether. The aqueous layer was acidified to pH2 with 10% KHSO₄ and extracted with EtOAc. The EtOAc layer was dried over Na₂SO₄, filtered and evaporated to give 1–5 as a white solid.

¹H NMR (300 MHz, CD₃OD) δ3.7 (d, 2H), 2.9 (t, 2H), 2.4 (m, 2H), 1.75 (m, 1H), 1.65 (m, 1H), 1.4 (d, 2H), 1.1 (s, 9H), 1.0–1.4 (m, 7H).

1 (S)-[2-(N-t-Butyloxycarbonylpiperidin-4-yl)ethyl]-2(S)-[methyl 3-(2(S)-butylsulfonylamino)propionate]cyclopropane dicarboxamide (1–7)

The acid 1–5 (0.017 g, 0.5 mmol) was dissolved in 1.5 mL acetonitrile and treated with diamine 1–6 (0.15 g, 0.54 mmol), triethylamine (0.22 mL, 1.58 mmol) and BOP reagent (0.38 g, 0.86 mmol) at room temperature for 18 hours. The reaction was concentrated, and the residue dissolved in EtOAc, washed with 10% KHSO₄ and brine and concentrated purification with flash chromatography on silica eluting with 60% acetone/hexanes yielded 1–7 as a white solid.

R_f (60% acetone/hexanes) 0.4. ¹H NMR (300 MHz, CD₃OD) δ8.4 (m, H), 8.1 (m, 1H), 4.2 (dd, 1H), 4.0 (d, 2H), 3.75 (s, 3H), 3.6 (m, 1H), 3.4 (m, 1H), 3.2 (m, 2H), 3.0 (t, 2H), 2.7 (m, 2H), 2.0 (t, 2H), 1.8–1.7 (m, 4H), 1.4 (s, 9H), 1.25 (t, 2H), 1.0 (m, 2H), 0.95 (t, 3H).

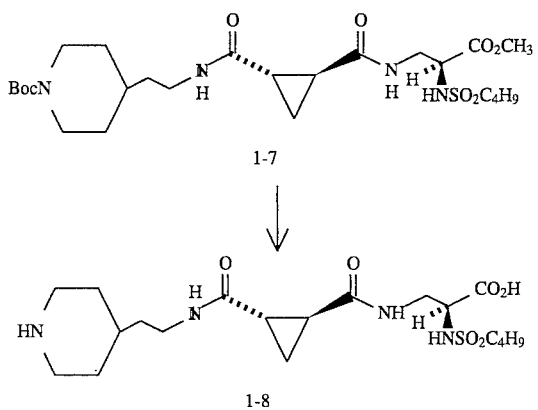

1(S)-[2-(Piperidin-4-yl)ethyl]-2(S)-[3-(2(S)-butylsulfonylamino)propionic acid]cyclopropane dicarboxamide (1–8)

Compound 1–7 (0.27 g, 0.48 mmol) was dissolved in 6 mL (1:1:1 THF/MeOH/H₂O) and treated with LiOH.H₂O (0.1 g, 2.38 mmol) for 30 minutes. The reaction was concentrated, the residue dissolved in H₂O and washed with EtOAc. The aqueous layer was acidified to pH2 with 10% KHSO₄ and extracted with EtOAc. The organic layer was dried with Na₂SO₄, filtered and concentrated. The resulting oil was dissolved in 7 mL EtOAc, cooled to –20° C. and the solution was saturated with HCl gas. The reaction was warmed to 0° C. for 40 minutes, then concentrated on the rotary evaporator at room temperature to yield a white solid. Flash chromatography on silica eluting with 9:1:1 EtOH/NH₄OH gave 1–8 as a white solid.

¹H NMR (300 MHz, D₂O) δδ 3.9 (dd, 1H), 3.7 (dd, 1H), 3.4 (d, 2H), 3.2–3.1 (m, 5H), 2.95 (t, 2H), 2.1–1.95 (m, 4H), 1.75 (m, 3H), 1.6–1.3 (m, 8H),0.9(t, 3H).

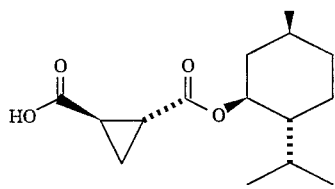

Mono-(1S,2R,5S)-(+)-menthyl-1(R),2(R)-cyclopropanedicarboxylate (1–9)

Bis-(1S,2R,5S)-(+)-menthyl (1R,2R)-cyclopropane dicarboxylate (*Org. Syn.* 67 p. 76–85) was treated as described for 1—1 to give 1–9 as a yellow oil.

R_f (97:3:1 CHCl₃/CH₃OH/HOAc) 0.2. ¹H NMR (300 MHz, CDCl₃) δ6.2 (bs, 1H), 4.6 (m, 1H), 2.1 (m, 2H), 1.9 (d, 1H), 1.8 (m, 1H), 1.6 (d, 2H), 1.4–1.3 (m, 4H), 1.0–0.7 (m, 3H), 0.84 (s, 3H), 0.82 (s, 3H), 0.68 (d, 3H).

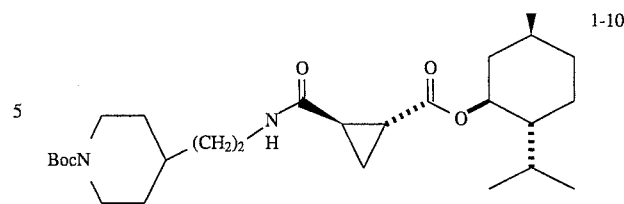

1 (S)-[(2-(N-t-Butyloxycarbonylpiperidin-4-yl)ethyl) acetamido]-2(S)-[(1S), (2R), 5(S)-(+)-menthylcarboxylatelcyclopropane (1–10)

Compound 1–9 was treated as described for 1–2 to give 1–10 as a white solid.

R_f (25% acetone/hexane) 0.29. ¹H NMR (300 MHz, CDCl₃) δ6.7 (t, 1H), 4.5 (m, 1H), 3.9 (bd, 2H), 3.2–3.0 (m, 2H), 2.6–24 (t, 2H), 2.0 (m, 1H), 1.9 (m, 2H), 1.6–1.7 (d, 2H), 1.3 (s, 9H), 1.2 (m, 6H), 1.0–0.7 (m, 8H), 0.78 (s, 3H), 0.76 (s, 3H), 0.62 (d, 3H).

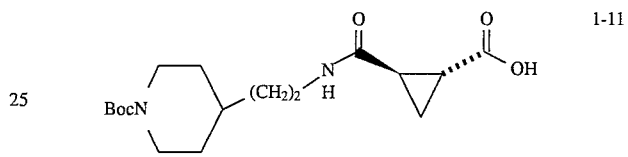

1(R)-[(2-(N-t-Butyloxycarbonylpiperidin-4-yl) ethyl)acetamido]-2-(R)-carboxycyclopropane (1–11)

Compound 1–10 was treated as described for 1–4 to give 1–11 as a white solid.

¹H NMR (300 MHz, CD₃OD) δ4.6–4.5 (d, 2H), 3.7 (t, 2H), 3.3–3.1 (t, 2H), 2.6–2.4 (m, 2H), 2.2 (d, 2H), 1.9 (s, 9H), 1.8-1.7 (m, 5H), 1.6 (m, 2H).

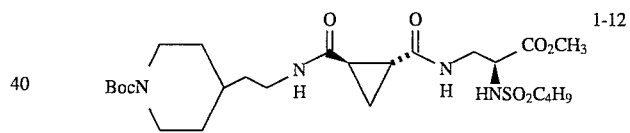

1 (R)-[2-(N-t-Butyloxycarbonylpiperidin-4-yl)ethyl]-2(R)-[methyl 3-(2(S)-butylsulfonylamino)propionate]cyclopropane dicarboxamide (1–12)

Compound 1–11 was treated as described for 1–5 to give 1–12 as a yellow oil.

R_f (50% acetone/hexane) 0.31. ¹H NMR (300 MHz, CD₃OD) δ4.2 (m, 1H), 4.0 (d, 2H), 3.7 (s, 3H), 3.5 (m, 2H), 3.2 (m, 2H), 3.0 (t, 2H), 2.75 (m, 2H), 2.0 (t, 2H), 1.7 (m, 4H), 1.4 (s, 9H), 1.2 (m, 2H), 1.0 (m, 2H), 0.9 (t, 3H).

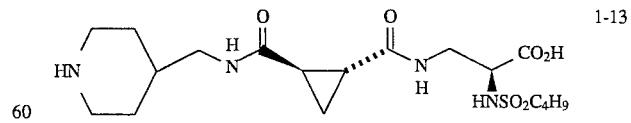

(S)- [2-(Piperidin-4-yl)ethyl]-2(S)-[3-(2(S)-butylsulfonylamino)propionic acid]cyclopropane dicarboxamide (1–13)

Compound 1–12 was treated as described for compound 1–8 to give 1–13 as a white solid.

¹H NMR (300 MHz, D₂O) δ 3.95 (m, 1H), 3.6–3.4 (m, 2H), 3.4 (d, 2H), 3.3 (m, 2H), 3.18 (t, 2H), 3.0 (t, 2H), 2.1 (t, 2H), 1.95 (d, 2H), 1.7 (m, 3H), 1.6–1.3 (m, 8H), 0.9 (t, 3H).

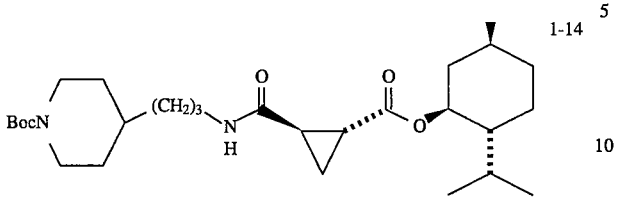

1(S)-[(3-(N-t-Butyloxycarbonylpiperidin-4-yl)propyl) acetamido]-2(S)-[(1(S),2(R),5(S))-(+)-menthylcarboxylate]cyclopropane (1–14)

Compound 1–9 was treated as for 1–10, utilizing 3-(4-N-tbutyloxycarbonyl piperidyl)propylamine 2–4, to give 1–14 as a colorless oil.

R_f (30% acetone/hexanes) 0.64 ¹H NMR (300 MHz, CDCl₃) δ6.0 (s, 1H), 4.6 (m, 1H), 4.0 (bs, 2H), 3.2 (m, 2H), 2.7 (bt, 2H), 2.1 (m, 1H), 1.9 (m, 3H), 1.7 (m, 4H), 1.6–1.2 (m, 10H), 1.45 (s, 9H), 1.1 (m, 4H), 0.9 (d, 6H), 0.76 (d, 3H).

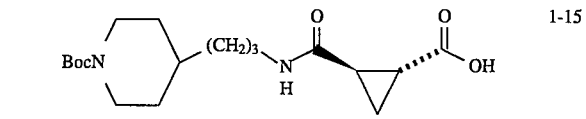

1(R)-[3-(N-t-Butyloxycarbonylpiperidin-4-yl)propyl) acetamido]-2(R)-carboxycyclopropane (1–15)

Compound 1–14 was treated as described for 1–11 to give 1–15 as a colorless oil.

¹H NMR (300 MHz, CD₃OD) δ8.2 (s, 1H), 3.9 (d, 2H), 3.0 (t, 2H), 2.6 (t, 2H), 1.95 (m, 1H), 1.8 (m, 1H), 1.6 (d, 2H), 1.4 (m, 2H), 1.3 (s, 9H), 1.2–1.0 (m, 5H), 0.9 (m, 2H).

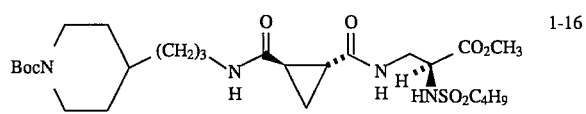

1(R)-[3-(N-t-Butyloxycarbonylpiperidin-4-yl)propyl]-2(R)-[methyl 3-(2(S)-butylsulfonylamino)propionate]cyclopropane dicarboxamide (1–16)

Compound 1–15 was treated an described for 1–12 to give 1–16 as a yellow oil.

R_f (50% acetone/hexanes) 0.27. ¹H NMR (300 MHz, CD₃OD) δ4.1 (m, 3H), 3.8 (s, 3H), 3.4–3.2 (m, 4H), 3.1 (t, 2H), 2.7 (t, 2H), 2.0 (m, 4H), 1.8 (m, 4H), 1.4 (s, 9H), 1.4 (m, 3H) 1.2 (m, 3H), 1.1 (m, 3H), 1.0 (t, 3H).

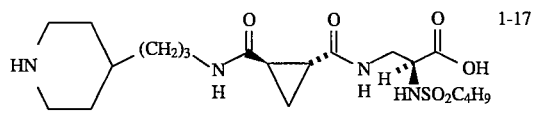

1(S)-[3-(Piperidin-4-yl)propyl]-2(S)-[3-(2(S)-butylsulfonylamino)propionic acid]cyclopropane dicarboxamide (1–17)

Compound 1–16 was treated as described for 1–12 to give 1–17 as a white solid.

R_f (9:1:1 EtOH/H₂O/NH₄OH) 0.26 ¹H NMR (300 MHz, D₂O) δ3.9 (m, 1H), 3.5 (m, 2H), 3.4 (d, 2H), 3.2 (m, 4H), 3.0 (t, 2H), 2.1 (m, 3H), 2.0 (d, 2H), 1.8 (m, 2H), 1.6 (m, 2H), 1.5–1.2 (m, 8H), 0.9 (t, 3H).

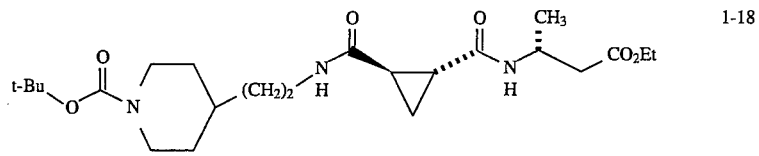

1(R)-[2-(N-t-Butyloxycarbonylpiperidin-4-yl) ethyl]-2(R)-[ethyl 3-(3(S)-methyl)propionate]cyclopropane dicarboxamide (1–18)

Compound 1–11 (0.26 g, 0.76 mmol) and ethyl 3-(3(S)m-ethyl)amino propionate (European Publication 512,831) (0.13 g, 0.77 mmole) were dissolved in acetonitrile and treated with triethylamine (0.33 mL, 2.4 mmole) and BOP reagent (0.62 g, 1.4 mmole) at room temperature. After stirring for 24 hours the reaction was concentrated, redissolved in ethyl acetate, washed with 10% KHSO₄ and brine, and concentrated. The residue was adsorbed to SiO₂ and chromatographed (50% acetone in hexanes) to give 1–18 as a white solid.

R_f (50% acetone/hexanes) 0.31. ¹H NMR (300 MHz, CD₃OD + CDCl₃) δ4.3 (m, 1H), 4.1 (g, 2H), 4.05 (d, 2H), 3.25 (m, 2H), 2.7 (t, 2H), 2.55 (dd, 1H), 2.45 (dd, 1H), 1.95 (m, 2H), 1.7 (bd, 2H), 1.46 (s, 9H), 1.3 (m, 2H), 1.1 (m, 2H).

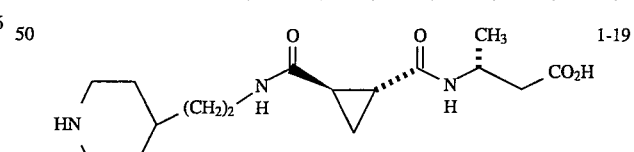

1(R)-[2-(Piperidin-4-yl)ethyl]-2(R)-[3-(3(S)-methyl)propionic acid]cyclopropane dicarboxamide (1–19)

Compound 1–18 was treated as described for 1–8 to give 1–19 as a white solid.

¹H NMR (300 MHz, D₂O) δ4.2 (dd, 1H), 3.4 (d, 2H), 3.25 (t, 2H), 3.0 (t, 2H), 2.4 (m, 2H), 2.0 (m, 4H), 1.6 (m, 1H), 1.5 (m, 2H), 1.4 (d, 2H), 1.3 (m, 2H), 1.2 (d, 3H).

SCHEME 2

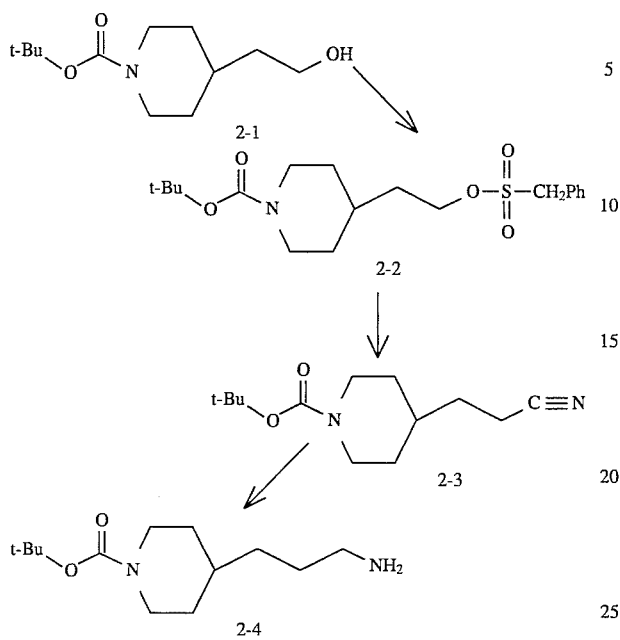

O-Benzylsulfonyl-N-(4-t-butyloxycarbonylpiperidyl)-2-ethyl alcohol (2—2)

N-(4-t-butyloxycarbonyl piperidyl)-2-ethyl alcohol (2–1, U.S. Pat. No. 5,294,616) (2 g, 8.7 mmole) was dissolved in 40 mL CH$_2$Cl$_2$, cooled to 0° C. and treated with triethylamine (1.6 mL, 11.5 mmole), α-toluene sulfonyl chloride (2.16 g, 11.3 mmole) and DMAP (0.1 g, 0.8 mmole). The reaction was warmed to room temperature and the solvent removed under reduced pressure. The residue was redissolved in ethyl acetate, washed with H$_2$O, NaHCO$_3$ and brine, dried over MgSO$_4$, filtered and concentrated to yield 2—2 as a yellow oil.

R$_f$ (50% EtOAc/hexanes) 0.55. $^1$H NMR (300 MHz, CDCl$_3$) δ7.4 (s, 5H), 4.3 (s, 2H), 4.0 (m, 2H), 2.6 (t, 2H), 1.5 (m, 3H), 1.4 (s, 9H), 1.0 (m, 2H).

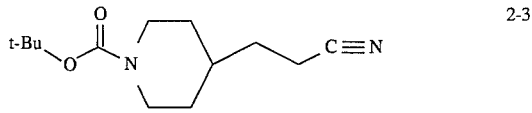

3(N-t-Butyloxycarbonylpiperidin-4-yl)propionitrile(2–3)

Compound 2—2 (3.2 g, 8.3 mmole) was dissolved in 5 mL DMSO and 1.18 g of potassium cyamide was added. The mixture was heated to 70° C. for two hours, then stirred at room temperature for 12 hours. The reaction was diluted with ether, and extracted with H$_2$O, dried with MgSO$_4$, filtered and concentrated to give 2–3 as a yellow oil.

$^1$H NMR (300 MHz, CDCl$_3$) δ4.1 (d, 2H), 2.7 (t, 2H) 2.4 (t, 2H), 1.6 (m, 5H), 1.45 (s, 9H), 1.1 (m, 2H).

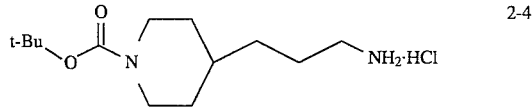

3-(N-t-Butyloxycarbonylpiperidin-4-yl)propylamine (2–4)

Compound 2–3 (0.89 g, 3.7 mmole) was dissolved in 2 mL CH$_2$Cl$_2$ and 25 mL EtOH and treated with PtO$_2$ (0.113 g, 0.49 mmole) and H$_2$ at 55 psi for 24 hours. The reaction was filtered and concentrated to give 2–4 as a white solid.

$^1$H NMR (300 MHz, 5% CD$_3$OD M CDCl$_3$) δ8.0 (bs, 2H), 4.1 (d, 2H), 2.9 (bs, 2H), 2.7 (t, 2H), 1.7 (m, 4H), 1.5 (s, 9H), 1.4–1.3 (m, 3H), 1.1 (m, 2H).

SCHEME 3

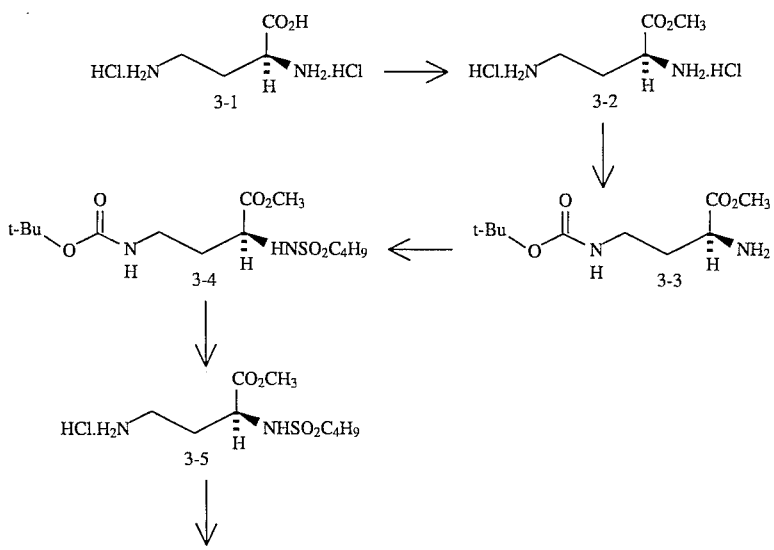

-continued
SCHEME 3

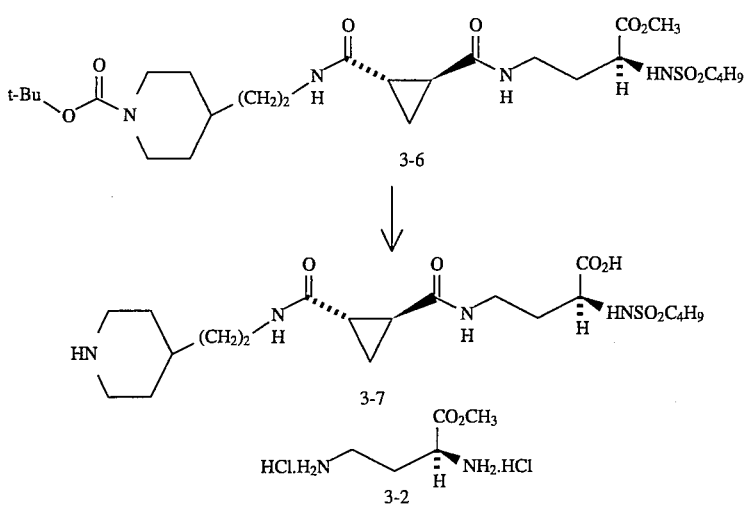

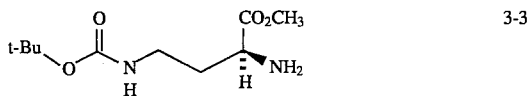

Methyl 2(S), 4-diaminobutyrate (3-2.)

Methanol (100 mL) was cooled to 0° C. and thionyl chloride (46.5 mL, 642 mmole) was added dropwise over 1 hr. Crushed 4,2(S) diamino butyrate (3-1, 5 g, 26.3 mmole, Schweizerhall) was added and the mixture was brought to reflux for three hours. The solvent and excess reagent were removed under reduced pressure to give 3-2 as a hygroscopic white foam.

$R_f$ (9:1:1 EtOH/H$_2$O/NH$_4$OH) 0.61. $^1$H NMR (400 MHz, CD$_3$OD) δ4.25 (t, 1H), 3.9 (s, 9H), 3.2 (m, 2H), 2.35 (m, 1H), 2.25 (m, 1H).

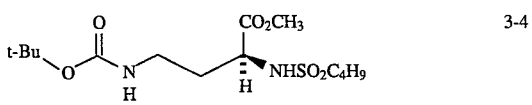

Methyl 2(S)-amino-4-(N-t-butyloxycarbonylamino)butyrate (3—3)

Compound 3-2 (1 g, 4.9 mmole) was crushed, suspended in CH$_2$Cl$_2$ and cooled to 0° C. Triethylamine (2 mL, 14.7 mmole) was added, followed by di-t-butyldicarbonate (0.96 g, 4.4 mmole) dissolved in CH$_2$Cl$_2$. After stirring for three hours the reaction was extracted with 10% KHSO$_4$ and the aqueous layer was washed with CH$_2$Cl$_2$. The pH of the aqueous layer was raised to 10–11 with sat. NaHCO$_3$ and NaOH solvent and extracted several times with CH$_2$Cl$_2$. The organic layer was dried with MgSO$_4$, filtered and concentrated to give 3—3 as an oil.

$R_f$ (5% CH$_3$OH/CHCl$_3$ sat. NH$_3$) 0.52. $^1$H NMR (400 MHz, CDCl$_3$) δ5.2 (bs, 1H), 3.7 (s, 3H), 3.5 (dd, 1H), 3.35 (m, 1H), 3.25 (m, 1H), 1.95 (m, 1H), 1.7 (m, 1H), 1.4 (s, 9H).

Methyl 2(S)-butylsulfonylamino-4-(N-t-butyloxycarbonylamino)-butyrate (3-4)

Compound 3—3 (0.5 g, 2.15 mmole) was suspended in 10 mL acetonitrile and treated successively with n-butanesulfonly chloride (0.31 mL, 2.39 mmole) and pyridine (0.20 mL, 2.47 mmole). After stirring at room temperature for 24 hours the solvent was removed, the residue was adsorbed onto silica and eluted using 25% acetone/hexanes to give 3-4 as a yellow oil.

$R_f$ (30% acetone/hexanes) 0.38. $^1$H NMR (300 MHz, CDCl$_3$) δ5.5 (d, 1H), 4.9 (s, 1H), 4.16 (m, 1H), 3.8 (s, 9H), 3.4 (m, 1H), 3.2 (m, 1H), 3.0 (t, 2H), 2.1 (m, 1H), 1.8 (m, 3H), 1.4 (s, 9H), 1.4–1.3 (m, 2H), 1.9 (t, 3H).

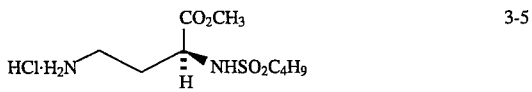

Methyl 2(S)-butylsulfonylamino-4-aminobutyrate hydrochloride (3-5)

Compound 3-4 (0.19 g, 0.54 mmole) was dissolved in ethyl acetate, cooled to −50° C. and treated with HCl gas. The solution was warmed to 0° C. for 45 minutes, then concentrated at room temperature to give 3-5 as a white solid.

$^1$H NMR (300 MHz, CDCl$_3$) δ8.0 (bs, 2H), 6.9 (d, 1H), 4.2 (bs, 1H), 3.8 (s, 3H), 3.3 (bs, 2H), 3.1 (t, 2H), 2.4 (m, 1H), 2.3 (m, 1H), 1.8 (m, 2H), 1.4 (m, 2H), 0.9 (t, 3H).

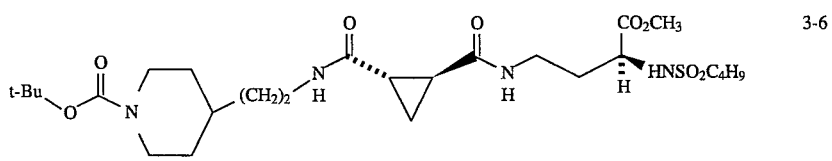

1(S)-[2-(N-t-Butyloxycarbonylpiperidin-4-yl)ethyl]-2(S)-[methyl4-(2( S )-butylsulfonylamino)butyl]cyclopropane dicarboxamide (3–6)

Compounds 1–5 (0.19 g, 0.56 mmole) and 3–5 (0.17 g, 0.59 mmole) were suspended in acetonitrile and treated with triethylamine (0.24 mL, 1.72 mmole) and BOP reagent (0.4 g, 0.9 mmole) at room temperature. After stirring for 18 hours the solution was concentrated, re-dissolved in ethyl acetate, washed with 10% $KHSO_4$ and brine, dried over $MgSO_4$, filtered and concentrated. Flash chromatography ($SiO_2$, 50% acetone/hexanes) gave 3–6 as a white solid.

$R_f$ (50% acetone/hexanes) 0.3. $^1H$ NMR (300 MHz, $CDCl_3$) and $CD_3OD$) δ4.15 (m, 1H), 4.05 (d, 2H), 3.75 (s, 3H), 3.25 (m, 4H), 3.0 (t, 2H), 2.7 (t, 2H), 2.0–1.7 (m, 8H), 1.7 (d, 2H), 1.45 (s, 9H) 1.25 (m, 3H), 1.1 (m, 2H), 0.95 (t, 3H).

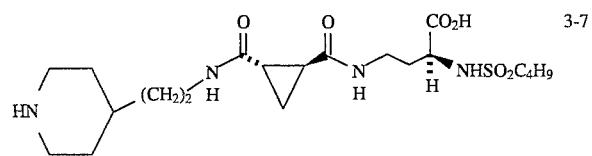

1(S)-[2-(Piperidin-4-yl)ethyl]-2(S)-[4-(2(S)-butylsulfonylamino)-butyryl]cyclopropane dicarboxamide (3–7)

Compound 3–6 was treated as described for 1–8 to give 3–7 as a white solid.

$R_f$ (9:1:1 $EtOH/H_2O/NH_4OH$). $^1H$ NMR (300 MHz, DMSO-$d_6$) δ8.3 (t, 1H), 8.2 (t, 1H), 6.4 (m, 1H), 3.4 (t, 1H), 3.3–3.0 (m, 6H), 2.95 (m, 2H), 2.75 (m, 2H), 1.85 (m, 1H), 1.8 (m, 1H), 1.75 (m, 2H), 1.7–1.45 (m, 4H), 1.35 (m, 3H), 1.2 (m, 2H), 1.0 (t, 2H), 0.85 (t, 3H).

$R_f$ (50% acetone/hexanes) 0.25. $^1H$ NMR (300 MHz, $CD_3OD$) 84.3 (t, 1H), 4.1 (d, 2H), 3.8 (s, 3H), 3.65 (dd, 1H), 3.55 (dd, 1H), 3.25 (t, 2H), 3.15 (t, 2H), 2.8 (t, 2H), 2.1 (m, 2H), 1.9 (m, 2H), 1.85 (d, 2H), 1.6–1.5 (m, 5H), 1.5 (s, 9H), 1.4 (t, 4H), 1.1 (m, 2H), 1.05 (t, 3H).

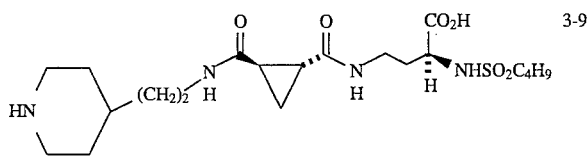

1(R)-[2-(Piperidin-4-yl)ethyl]-2(R)-[4-(2(S)-butylsulfonylamino)-butanoic acid]cyclopropane dicarboxamide (3–9)

Compound 3–8 was treated as described for 1–8 to give 3–9 as a white solid.

$R_f$ (:1:1 $EtOH/H_2O/NH_4OH$) 0.16. $^1H$ NMR (400 MHz, $D_2O$) δ3.65 (dd, 1H), 3.45 (m, 3H), 3.13 (m, 3H), 3.0 (t, 2H), 2.83 (t, 2H), 1.9 (m, 2H), 1.8 (m, 2H), 1.7–1.5 (m, 4H), 1.4 (dd, 2H), 1.3–1.2 (m, 5H), 1.35 (m, 2H), 0.75 (t, 3H).

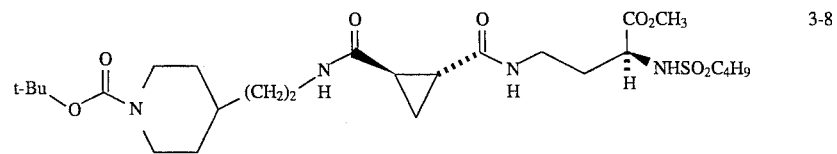

1(R)-[2-(N-t-Butyloxycarbonylpiperidin-4-yl)ethyl]-2(R)-[methyl 4-(2(S)-butylsulfonylamino)butyryl]cyclopropane dicarboxamide (3–8)

Compound 1–11 was treated as described for 3–6 to give 3–8 as a yellow oil.

SCHEME 4

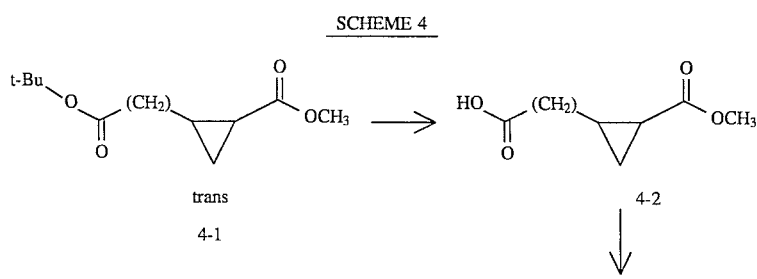

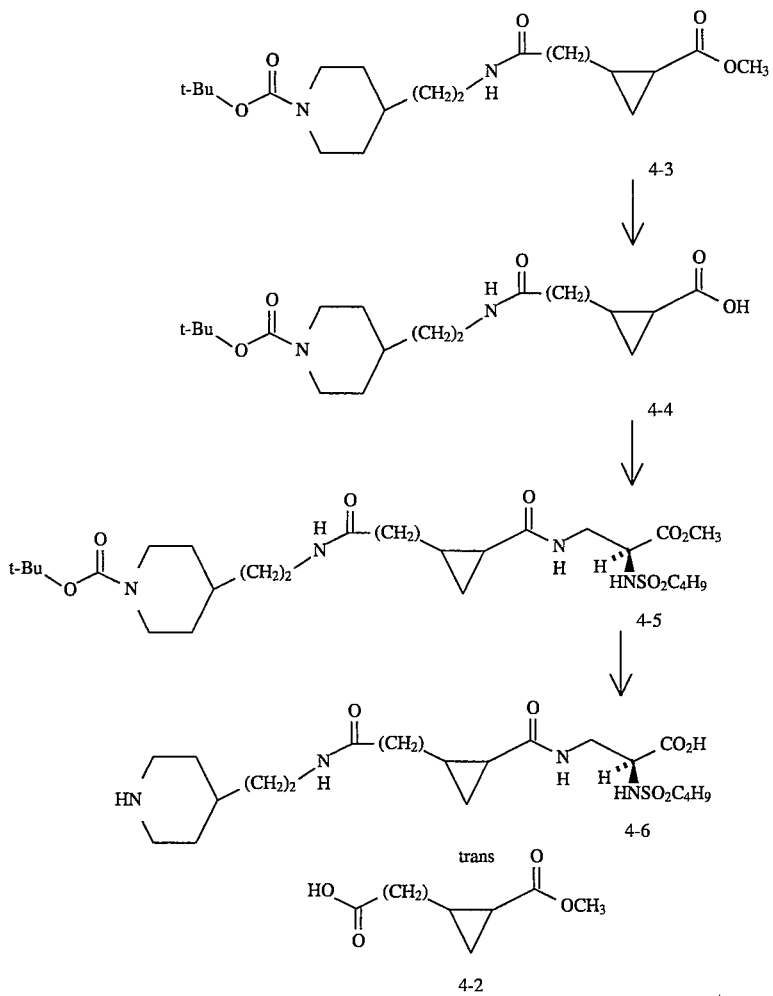

D,L-Trans-Methyl 2-carboxymethylcyclopropane carboxylate (4-2)

D,L-trans-methyl (t-butyl 2-carboxymethyl)cyclopropane carboxylate (4–1) (*Tet. Lett.* 1723, 1985) (2.08 g, 9.7 mmole) was dissolved in ethyl acetate, cooled to −50° C. and treated with HCl. The reaction was warmed to 0° C. for one hour, then the solvent was removed under reduced pressure at room temperature. The residue was dissolved in water, extracted with ethyl acetate. The organic layer was dried over $Na_2SO_4$, filtered and evaporated to give 4–2 as a dark yellow oil. $^1H$ NMR (300 MHz, $CD_3OD$) δ3.23 (s, 3H), 1.95 (dd, 1H), 1.85 (dd, 1H), 1.2 (m, 1H), 1.15 (m, 1H), 0.8 (m, 1H), 0.43 (m, 1H).

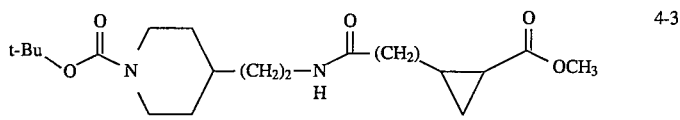

4-3

D,L-Trans-1-[((N-t-Butyloxycarbonylpiperidin-4-yl)ethylacetamido)methyl]-2-methoxycarbonylcyclopropane (4-3)

Compound 4-2 (0.22 g, 1.4 mmole) was dissolved in 7 mL acetonitrile and treated with 1-3 (0.29 g, 1.3 mmole), triethylamine (0.46 mL, 3.3 mmole) and BOP reagent (0.91 g, 2.05 mmole) at room temperature for 24 hours. The reaction was concentrated, re-dissolved in ethyl acetate, washed with 10% $KHSO_4$ and brine, and concentrated. The residue was adsorbed to silica and chromatography (40% acetone/-hexanes) to give 4-3 as a yellow oil.

$R_f$ (50% acetone/hexanes) 0.34. $^1H$ NMR (300 MHz, $CD_3OD + CDCl_3$) δ4.05 (bd, 2H), 3.6 (s, 3H), 3.25 (t, 2H), 2.7 (t, 2H), 2.2 (m, 2H), 1.65 (bd, 2H), 1.55 (m, 4H), 1.45 (s, 9H), 2.25 (m, 2H), 1.1 (m, 2H), 0.9 (m, 1H).

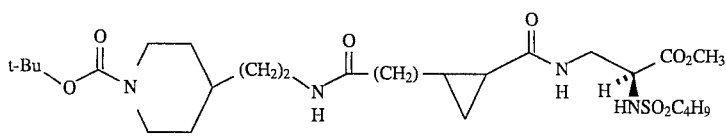

D,L-Trans-1-[((N-t-Butyloxycarbonylpiperidin-4-yl]ethyl-acetemido)-methyl]- 2-N-[methyl 3-(2(S)-butylsulfonylamino)-propionate]-cyclopropane carboxamide (4-5)

Compound 4-3 was treated as described for 1-4 to give 4-4 as a colorless oil Compound 4—4 (0.27 g, 0.76 mmole) was dissolved in 5 mL acetonitrile and treated with 1-6 (0.26 g, 0.94 mmole), triethylamino (0.32 mL, 2.3 mmole) and BOP reagent (0.63 g, 1.4 mmole) at room temperature for 24 hours. The solution was evaporated, re-dissolved in ethyl acetate, washed with 10% KHSO$_4$ and brine and concentrated. The residue was adsorbed to silica and eluted with 60% acetone/hexanes to give 4–5 as a white solid.

$R_f$ (60%) acetone/hexanes) 0.38. $^1$H NMR (300 MHz, CDCl$_3$) δ7.1 (bs, 1H), 6.6 (bs, 1H), 6.2 (bs, 1H), 4.2 (bs, 1H), 4.0 (bd, 2H), 3.8 (s, 3H), 3.7–3.5 (m, 3H), 3.25 (bs, 2H), 3.05 (bs, 2H), 2.7 (m, 2H), 2.3 (m, 1H), 2.2 (m, 1H), 1.75 (bs, 2H), 1.7 (bs, 2H), 1.45 (s, 9H), 1.5-1.4 (m, 5H), 1.2–1.0 (m, 4H), 0.95 (t, 3H), 0.75 (bs, 1H).

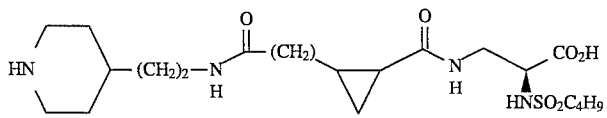

D,L-Trans-1-[((Piperidin-4-yl)ethylacetamido)methyl]-2-N-[3-(2(S)-butylsulfonylamino)propionic acid] cyclopropane carboxamide (4–6)

Compound 4–5 was treated as described for 1–8 to give 4–6 as a white solid.

$^1$H NMR (300 MHz, D$_2$O) δ3.9 (m, 1H), 3.6 (m, 1H), 3.4 (bd, 2H), 3.25 (m, 3H), 3.15 (m, 2H), 2.95 (t, 2H), 2.2 (m, 2H), 0.95 (bd, 2H), 1.7 (m, 2H), 1.6–1.3 (m, 10H), 1.1 (m, 1H), 0.9 (t, 3H).

SCHEME 5

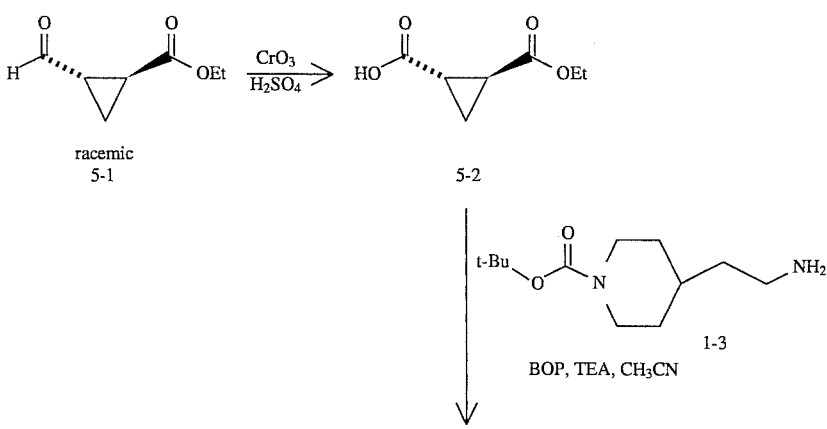

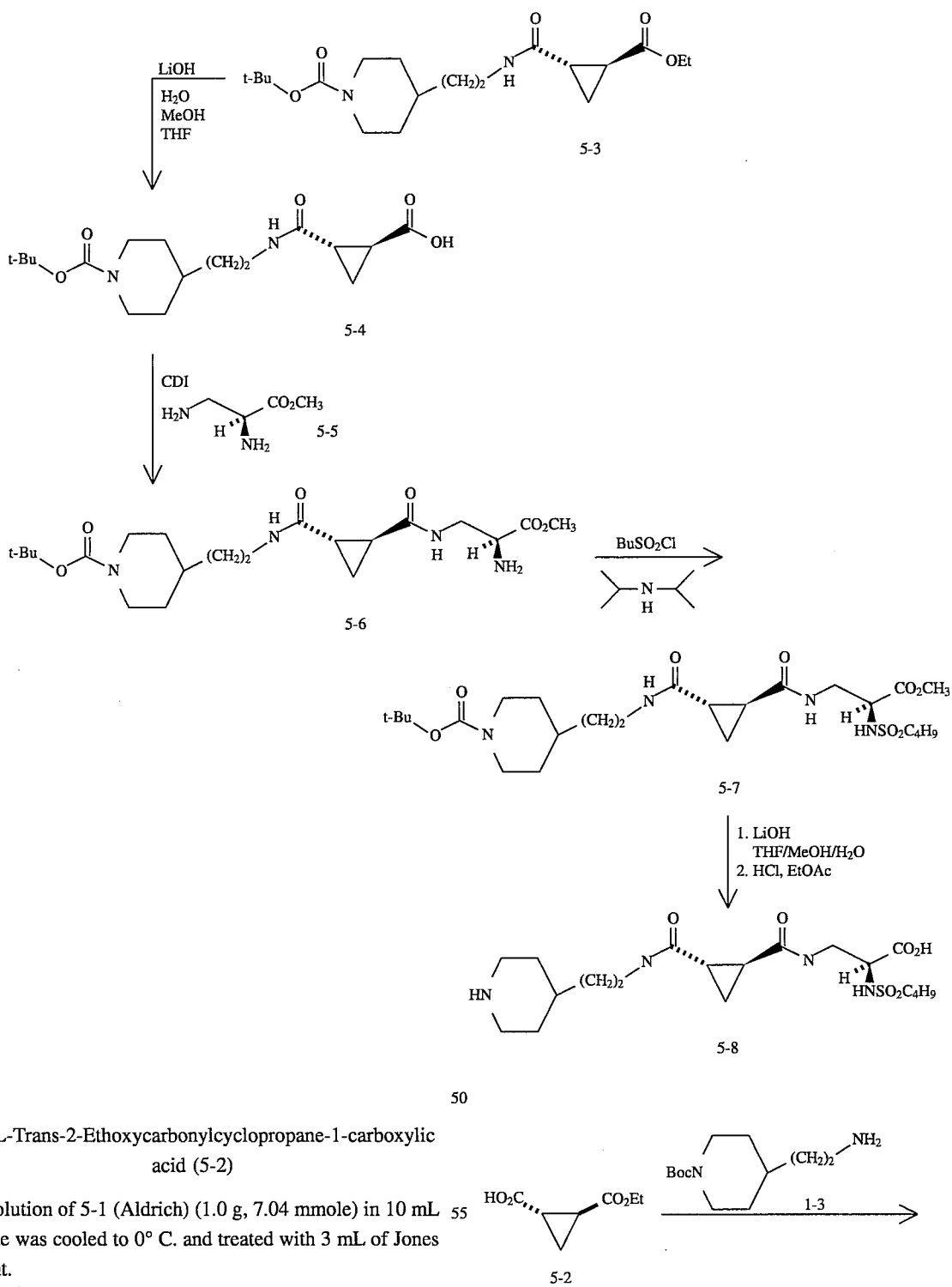

D,L-Trans-2-Ethoxycarbonylcyclopropane-1-carboxylic acid (5-2)

A solution of 5-1 (Aldrich) (1.0 g, 7.04 mmole) in 10 mL acetone was cooled to 0° C. and treated with 3 mL of Jones reagent.

The reaction was quenched with saturated NaHCO$_3$, filtered and the resulting aqueous solution was extracted and EtOAc, acidified to pH2 with 10% HCl and extracted with EtOAc. The second EtOAc extracted was concentrated to yield to 5-2 as a pale green oil.

$^1$H NMR (300 MHz, CD$_3$OD) δ4.8 (g, 2H), 2.75 (m, 2H), 2.05 (t, 2H), 1.9 (t, 3H).

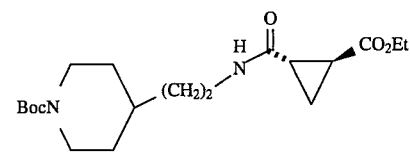

D,L-Trans-1-[(2-(N-t-Butyloxycarbonylpiperidin-4-yl)ethyl)acetamido]-2-ethoxycarbonylcyclopropane carboxamide (5-3)

A solution of 5-2 (0.3 g, 1.9 mmol) in 10 mL CH$_3$CN was treated with 1–3 (0.44 g, 1.9 mmol), triethylamine (0.8 mL, 5.7 mmol) and BOP reagent 1.3 g (2.9 mmol) at room temperature for 18 hours. The reaction was concentrated, dissolved in EtOAc, extracted, with 10% KHSO$_4$ and brine and concentrated. Flash chromatography on silica eluting with EtOAc(1)/Hexane(4) gave 5-3 as a pale yellow oil.

R$_f$ (20% EtOAc/Hexanes) 0.33. $^1$H NMR (300, CDCl$_3$) δ6.1 (s, 1H), 4.1 g (2H), 4.05 (bd, 2H), 3.3 (m, 2H), 2.7 (t, 2H), 2.1 (m, 1H), 1.95 (m, 1H), 1.7 (d, 2H), 1.6 (s, 9H), 1.6-1.0 (m, 5H), 1.3 (t, 3H).

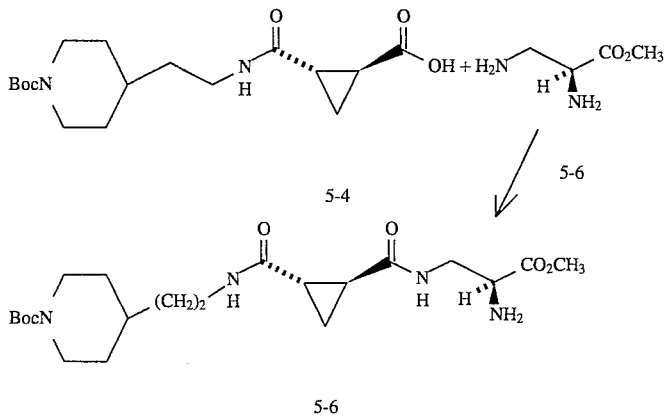

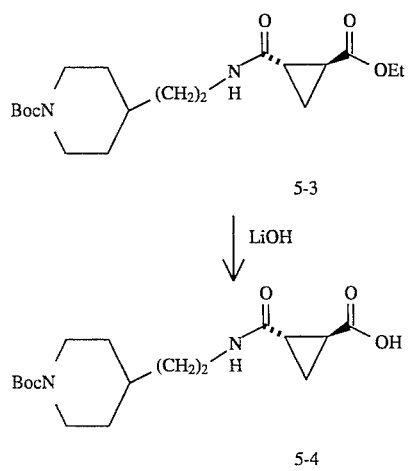

D,L-Trans-1-[(2-(Piperidin-4-yl)ethyl)acetamido]-2-carboxycyclopropane (5-4)

Compound 5-3 (0.38 g, 1 mmol) as dissolved in a 1:1:1 mixture of THF/MeOH/H$_2$O (total 21 mL) and treated with LiOH.H$_2$O (0.25 g, 5.8 mmol). After 20 min. the reaction was concentrated, and the residue dissolved in H$_2$O, acidified to pH2 with 10% KHSO$_4$ and extracted with EtOAc. The organic layers were dried with NaSO$_4$, filtered and concentrated to give 5-4 as a white solid.

$^1$H NMR (300 MHz, CD$_3$OD) δ4.1 (d, 2H), 3.1 (m, 2H), 2.8 (m, 2H), 2.1 (m, 1H), 1.95 (m, 1H), 1.75 (d, 2H), 1.45 (s, 9H), 1.5-1.2 (m, 5H), 1.1 (m, 2H).

D,L-Trans 1-[2(N-t-Butyloxycarbonylpiperidin-4-yl) ethyl]-2-[3-(Methyl 2(S)-amino)propionate ]cyclopropane dicarboxamide (5–6)

A solution of 5-4 (0.29 g, 0.86 mmol) in 7 mL DMF was treated with carbonyl diimazole (0.15 g, 0.94 mmol), N-methyl morpholine (0.6 mL, 5. mmol), and diamine 5—5 (0.4 g, 1.8 mmol, obtained from treatment of L-2,3-diaminopropanoic acid with thionyl chloride in methanol) at room temperature for 18 hours. The reaction was concentrated in vacuo, and the residue was dissolved in 10% KHSO$_4$ and washed with EtOAc. The aqueous layer was basified to pH 10 with NaOH and extracted with EtOAc. The organic layers were concentrated and purified by flash chromatography on silica gel eluting with 5% MeOH/CHCl$_3$ saturated with ammonia to give 5–6 as a yellow oil.

R$_f$ (5% MeOH/CHCl$_3$ sat. NH$_3$) 0.25. $^1$H NMR (300 MHz, CD$_3$OD) δ3.95 (d, 2H), 3.6 (s, 3H), 3.45 (m, 1H), 3.35 (s, 2H), 3.1 (t, 2H), 2.6 (m, 2H), 1.9 (m, 2H), 1.6 (d, 2H), 1.35 (s, 9H), 1.3–1.9 (m, 7H).

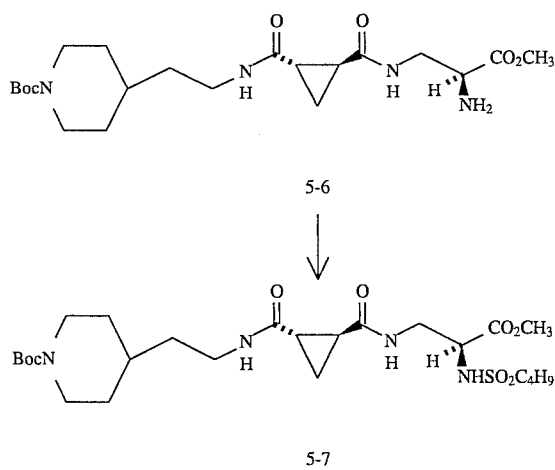

D,L-Trans-1-[2-(N-t-Butyloxycarbonylpiperidin-4-yl) ethyl]-2-[3-Methyl 2(S)-butylsulfonylamino)prioionate]cyclopropane dicarboxamide (5–7)

Compound 5–6 (0.28 g, 0.64 mmol) was dissolved in 5 mL CHCl₃ and treated with Diisopropylethylamine (0.32 mL, 1.9 mmol) and n-Butylsulfonyl chloride (0.1 mL, 0.77 mmol). After stirring for 18 hours, an additional 0.1 mL of n-Butylsulfonyl chloride was added and the reaction was heated to reflux for 24 hours. The reaction was concentrated and purified by chromatography on silica eluting with 50% acetone/hexanes to give 5–7 as a yellow oil.

$R_f$ (10% MeOH/CHCl₃ saturated with NH₃) 0.2. ¹H NMR (300 MHz, CDCl₃) δ7.8 (s, 1H), 7.1 (s, 1H), 4.35 (m, 1H), 4.15 (m, 2H), 3.75 (m, 2H), 3.5 (s, 3H), 3.35 (m, 2H), 3.1 (m, 2H), 2.7 (m, 2H), 2.1 (m, 2H), 1.9–1.7 (m, 4H), 1.6 (s, 9H), 1.5-1.1 (m, 9H), 1.0 (t, 3H).

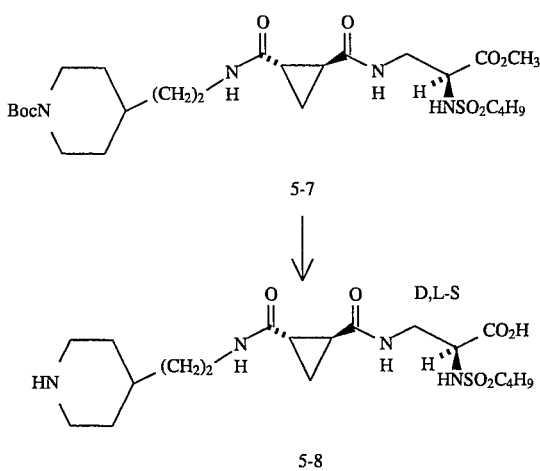

D,L-Trans-1-[2-(Piperidin-4-yl)ethyl]-2-[3-(2(S)-butylsulfonylamino)-propionic acid]cyclopropane dicarboxamide (5–8)

Compound 5–7 was treated with LiOH in THF/MeOH/H₂O and then with HCl/EtOAc as described for 1–8 to yield 5–8 as a white solid.

$R_f$ (9:1:1 EtOH/H20/NH4OH) 0.32. ¹H NMR (300 MHz, D₂O) δ3.84 (m, 1H), 3.6 (m, 1H), 3.3 (m, 1H), 3.25 (d, 2H), 3.05 (m, 2H), 3.02 (m, 2H), 2.83 (t, 2H), 1.95 (m, 2H), 1.83 (d, 2H), 1.6 (m, 3H), 1.4–1.2 (m, 8H), 0.8 (t, 3H).

The compounds of the present invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intrapefitoneal, subcutaneous, or intramusculsar form, all using forms well known to those of ordinary skill in the pharmaceutical arts. An effective but non-toxic amount of the compound desired can be employed as an anti-aggregation agent.

Compounds of the invention may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. Compounds of this invention may be administered to these surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between gp IIb/IIIa on the platelet membranes and fibrinogen adsorbed to the surface of the circuit. (Gluszko et al., Amer. J. Physiol., 252(H), 615–621 (1987)). Platelets released from artificial surfaces show impaired hemostatic function. Compounds of the invention may be administered to prevent adhesion.

Other applications of these compounds include prevention of platelet thrombosis, thromboembolism and reocclusion during and after s thrombolytic therapy and prevention of platelet thrombosis, thromboembolism and reocclusion after angioplasty or coronary artery bypass procedures. They may also be used to prevent myocardial infarction.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the present invention, when used for the indicated effects, will range between about 0.01 mg per kg of body weight per day (mg/kg/day) to about 100 mg/kg/day and preferably 0.01–100 mg/kg/day and most preferably 0.01–20 mg/kg/day. Intravenously, the most preferred doses will range from about 1 to about 10 mg/kg/minute during a constant rate infusion. Advantageously, compounds of the present invention may be administered in divided doses of two, three, or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a s transdermal delivery system, the dosage administration will, or course, be continuous rather that intermittent throughout the dosage regime.

In the methods of the present invention, the compounds herein described in detail can form the active ingredient, and are typically administered in admixture with suitable pharmaceutical diluents, excipients or carders (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carder such as lactose, starch, sucrose, glucose, methyl cellulose, magnesium stearate, dicalcium phosphate, calcium sulfate, mamnitol, sorbitol and the like; for oral administration in liquid form, the oral drug components can be combined with any oral, non-toxic, pharmaceutically acceptable inert carder such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweetners, natural and synthetic gums such as acacia, tragacanth or sodium alginate, carboxymethylkcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The compounds of the present invention can also be co-administered with suitable anticoagulation agents or thrombolytic agents such as plasminogen activators or streptokinase to achieve synergistic effects in the treatment of various vascular pathologies. They may also be combined with heparin, aspirin, or warfarin.

Platelet aggregation is measured at 37° C. in a Chronolog aggregometer. The reaction mixture contains gel-filtered human platelets ($2 \times 10^8$ per ml), fibrinogen (100 micrograms per ml (ug/ml)), $Ca^{2+}$ (1 mM), and the compound to be tested. The aggregation is initiated by adding 10 mM ADP 1 minute after the other components are added. The reaction is then allowed to proceed for at least 2 minutes. The extent of inhibition of aggregation is expressed as the percentage of the rate of aggregation observed in the absence of inhibitor. The $IC_{50}$ is the dose of a particular compound inhibiting aggregation by 50% relative to a control lacking the compound.

The novel compounds of the present invention were prepared according to the procedure of the following examples. The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

In addition to the following preparative procedures, several examples of in vitro bioactivity of compounds within the scope of the present invention are indicated. To illustrate, one test which is used to evaluate fibrinogen receptor antagonist activity is based on evaluation of inhibition of ADP-stimulated platelets. Aggregation requires that fibrinogen bind to and occupy the platelet fibrinogen receptor site. Inhibitors of fibrinogen binding inhibit aggregation. In the ADP-stimulated platelet aggregation assay used to determine inhibition associated with the compounds claimed in the instant invention, human platelets are isolated from fresh blood, collected into acid citrate/dextrose o by differential centrifugation followed by gel filtration on Sepharose 2B in divalent ion-free Tyrode's buffer (pH 7.4) containing 2% bovine serum albumin.

THERAPEUTIC TREATMENT

Compounds of the invention may be administered to patients where inhibition of human or mammalian platelet aggregation or adhesion is desired.

Compounds of the invention are useful in inhibiting platelet aggregation and thus, they may find utility in surgery on peripheral arteries (arterial grafts, carotid endaterectomy) and in cardiovascular surgery where manipulation of arteries and organs, and/or the interaction of platelets with artificial surfaces, leads to platelet aggregation and consumption. The aggregated platelets may form thrombi and thromboemboli. Compounds of the invention may be administered to these surgical patients to prevent the formation of thrombi and thromboemboli.

Using methods described herein, as well as others that are known in the literature, the following compounds may be prepared and are descriptive of the present invention:

What is claimed is:

1. A compound having the formula

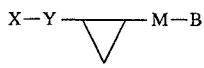

and pharmaceutically acceptable salts thereof, and esters thereof, wherein X is

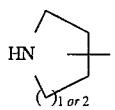

M is chosen from

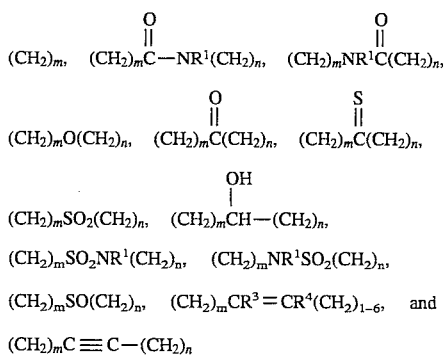

Y is chosen from

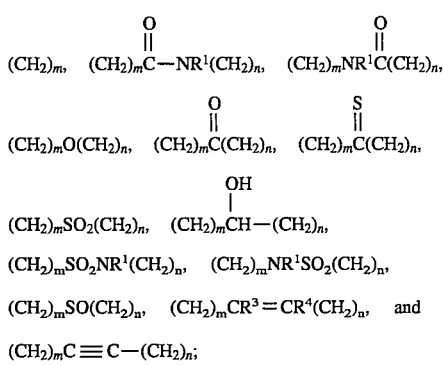

m and n, wherein m is independently selected for Y and M, are integers independently chosen from 0–6;
B is chosen from:

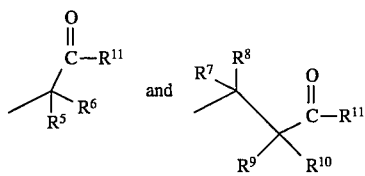

wherein $R^5$, $R^6$, $R^7$, and $R^8$ are independently chosen from:
hydrogen,
flourine,
$C_{1-8}$ alkyl,
hydroxyl,
hydroxy $C_{1-6}$ alkyl,
carboxy $C_{0-6}$ alkyl,
$C_{1-6}$ alkyloxy $C_{0-6}$ alkyl,
$C_{1-6}$ alkylcarbonyl $C_{0-6}$ alkyl,
$C_{3-8}$ cycloalkyl $C_{0-6}$ alkyl,
aryl $C_{0-6}$ alkylcarbonyl $C_{0-6}$ alkyl,
aryl $C_{0-6}$ alkyl,
$C_{1-6}$ alkylcarbonyloxy $C_{0-6}$ alkyl,
$C_{0-6}$ alkylamino $C_{0-6}$ alkyl,
aryl $C_{0-6}$ alkylamino $C_{0-6}$ alkyl,
$C_{0-6}$ dialkylamino $C_{0-6}$ alkyl,
aryl $C_{0-6}$ alkylcarbonyloxy $C_{0-6}$ alkyl,
$C_{1-8}$ alkylsulfonylamino $C_{0-6}$ alkyl,
$C_{1-6}$ alkylaminocarbonyloxy $C_{0-6}$ alkyl,
aryl $C_{0-6}$ alkylaminocarbonyloxy $C_{0-6}$ alkyl,
aryl $C_{0-6}$ alkylsulfonylamino $C_{0-6}$ alkyl,
$C_{1-8}$ alkyloxycarbonylamino $C_{0-8}$ alkyl,
aryl $C_{0-8}$ alkyloxycarbonylamino $C_{0-8}$ alkyl,
$C_{1-8}$ alkylcarbonylamino $C_{0-6}$ alkyl,
aryl $C_{0-6}$ alkylcarbonylamino $C_{0-6}$ alkyl,
$C_{0-8}$ alkylaminocarbonyl $C_{0-6}$ alkyl,
aryl $C_{0-8}$ alkylaminocarbonyl $C_{0-6}$ alkyl,
$C_{1-8}$ alkylaminocarbonylamino $C_{0-6}$ alkyl,
aryl $C_{0-8}$ alkylaminocarbonylamino $C_{0-6}$ alkyl,
$C_{0-8}$ alkylaminosulfonylamino $C_{0-6}$ alkyl,
aryl $C_{0-8}$ alkylaminosulfonylamino $C_{0-6}$ alkyl,
$C_{1-6}$ alkylsulfonyl $C_{0-6}$ alkyl,
aryl $C_{0-6}$ alkylsulfonyl $C_{0-6}$ alkyl,
aryl $C_{0-6}$ alkylcarbonyl $C_{0-6}$ alkyl,
$C_{1-6}$ alkylthiocarbonylamino $C_{0-6}$ alkyl,
aryl $C_{0-6}$ alkylthiocarbonylamino $C_{0-6}$ alkyl,
wherein alkyl groups may be unsubstituted or substituted with one or more substituents selected from
hydrogen,
$C_{1-10}$ alkyl,
aryl $C_{0-8}$ alkyl,
oxo,
thio,
amino $C_{0-8}$ alkyl, $C_{1-3}$ acylamino $C_{0-8}$ alkyl,
$C_{1-6}$ alkylamino $C_{0-8}$ alkyl,
$C_{1-6}$ dialkylamino $C_{0-8}$ alkyl,
$C_{1-4}$ alkoxy $C_{0-6}$ alkyl,
carboxy $C_{0-6}$ alkyl, $C_{1-3}$ alkoxycarbonyl $C_{0-6}$ alkyl,
carboxy $C_{0-6}$ alkyloxy and
hydroxy $C_{0-6}$ alkyl;
wherein $R^9$ and $R^{10}$ are independently chosen from:
hydrogen, with the proviso that $R^9$ and $R^{10}$ cannot both be hydrogen,
$C_{1-8}$ alkyisulfonylamino $C_{0-6}$ alkyl,
aryl $C_{0-6}$ alkylsulfonylamino $C_{0-6}$ alkyl,
$C_{0-8}$ alkylaminosulfonylamino $C_{0-6}$ alkyl,
aryl $C_{0-8}$ alkylaminosulfonylamino $C_{0-6}$ alkyl,
wherein alkyl groups may be unsubstituted or substituted with one or more substituents selected from
hydrgen,
$C_{1-10}$ alkyl,
aryl $C_{0-8}$ alkyl,
oxo,
thio,
amino $C_{0-8}$ alkyl, $C_{1-3}$ acylamino $C_{0-8}$ alkyl,
$C_{1-6}$ alkylamino $C_{0-8}$ alkyl,
$C_{1-6}$ dialkylamino $C_{0-8}$ alkyl,
$C_{1-4}$ alkoxy $C_{0-6}$ alkyl,
carboxy $C_{0-6}$ alkyl, $C_{1-3}$ alkoxycarbonyl $C_{0-6}$ alkyl,
carboxy $C_{0-6}$ alkyloxy and
hydroxy $C_{o-6}$ alkyl; and
$R^{11}$ is chosen from:
hydroxy,
$C_{1-8}$ alkyloxy,
aryl $C_{0-6}$ alkyloxy,
$C_{1-8}$ alkylcarbonyloxy $C_{1-4}$ alkyloxy,
aryl $C_{1-8}$ alkylcarbonyloxy $C_{1-4}$ alkyloxy,
2. A compound of claim 1 selected from the group consisting of:

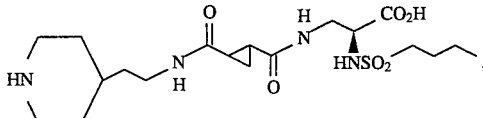

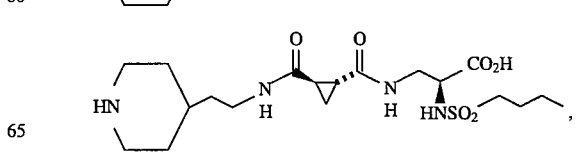

-continued

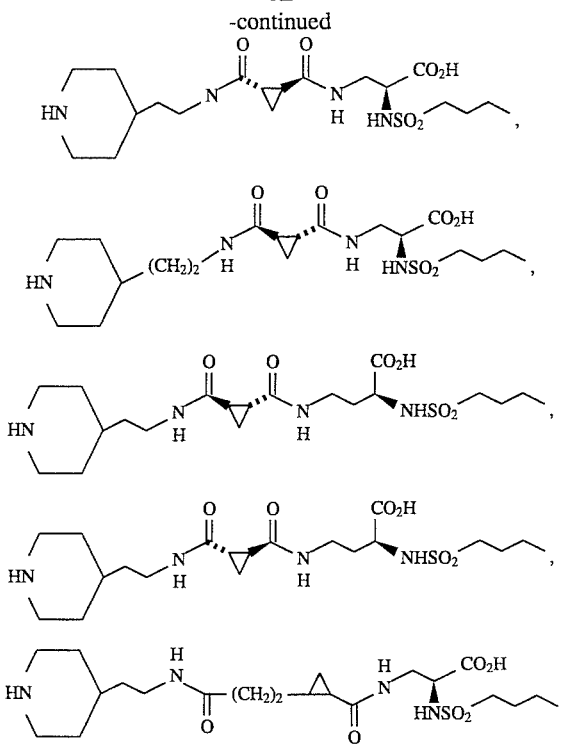

and pharmaceutically acceptable salts thereof, and esters thereof.

3. A compound of claim 1 for use in inhibiting the binding of fibrinogen to blood platelets, inhibiting the aggregation of blood platelets, or preventing thrombus or embolus formation in a mammal.

4. A composition for inhibiting the binding of fibrinogen to blood platelets in a mammal, comprising a compound of claim 1 and a pharmaceutically acceptable carrier.

5. A method for inhibiting the binding of fibrinogen to blood platelets in a mammal, comprising administering to the mammal an binding effective amount of a composition of claim 4.

6. A compound of claim 2 for use in inhibiting the binding of fibrinogen to blood platelets, inhibiting the aggregation of blood platelets, or preventing thrombus or embolus formation in a mammal.

7. A composition for inhibiting the binding of fibrinogen to blood platelets, in a mammal, comprising a compound of claim 2 and a pharmaceutically acceptable carrier.

8. A method for inhibiting the binding of fibrinogen to blood platelets in a mammal, comprising administering to the mammal an antifibrinogenic binding effective amount of a composition of claim 7.

* * * * *